US006503888B1

(12) United States Patent
Kaplitt et al.

(10) Patent No.: US 6,503,888 B1
(45) Date of Patent: *Jan. 7, 2003

(54) AAV-MEDIATED DELIVERY OF DNA TO CELLS OF THE NERVOUS SYSTEM

(75) Inventors: Michael G. Kaplitt, New York, NY (US); Matthew J. During, Weston, CT (US)

(73) Assignees: The Rockefeller University, New York, NY (US); Yale University, New Haven, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/548,176

(22) Filed: Apr. 13, 2000

Related U.S. Application Data

(63) Continuation of application No. 08/467,044, filed on Jun. 6, 1995, now Pat. No. 6,180,613, which is a continuation-in-part of application No. 08/227,319, filed on Apr. 13, 1994, now abandoned.

(51) Int. Cl.⁷ .............................................. A01N 43/04
(52) U.S. Cl. ...................... 514/44; 435/320.1; 435/455; 435/456
(58) Field of Search .................... 514/44; 435/320.1, 435/455, 456, 235.1

(56) References Cited

U.S. PATENT DOCUMENTS

| | | | |
|---|---|---|---|
| 4,797,368 A | 1/1989 | Carter et al. | 435/320.1 |
| 5,139,941 A | 8/1992 | Muzyczka et al. | 435/456 |
| 5,173,414 A | 12/1992 | Lebkowski et al. | 435/964 |
| 5,252,479 A | 10/1993 | Srivastava et al. | 435/235.1 |
| 6,180,613 B1 * | 1/2001 | Kaplitt et al. | 514/44 |

FOREIGN PATENT DOCUMENTS

| | | |
|---|---|---|
| WO | WO 94/13788 | 6/1994 |
| WO | WO 95/13365 | 5/1995 |
| WO | WO 95/13391 | 5/1995 |
| WO | WO 95/13392 | 5/1995 |

OTHER PUBLICATIONS

Akli et al (1993) *Nature Genetics* 3:224–228.
Allen et al. (1987) Proc. Natl. Acad. Sci. USA 84:2532–6.
Andersen et al. (1992) Human Gene Therapy 3:487–99.
Bajocchi et al. (1993) 3:229–234.
Breakefield et al. (1991) The New Biologist 3:203–18.
Chatterjee et al., 1993, Methods 5:51–9.
Chatterjee, et al., Science, 258:1485–88 (1992).
Chen et al., 1991, J. Cellular Biochem. 45:252–57.
Davidson et al (1993) Nature Genetics 3:219–223.
de Fiebre et al. (1992) Soc. Neurosci. Abst. 18:1–2 (Abstract 331.2).
de Fiebre et al. (1994) Neurochem. Res. 19:643–8.
de Fiebre et al. (1993) Neurochem. Res. 18:1089–94.
During et. al. (1994) *Abstr. Soc. Neurosci.* 20, 1465 (Abs. 602.10).
During et. al. (1994) Science 266:1399–403.
During et al., 1998, Gene Therapy 5:820–7.
Federoff et al. (1992) Proc. Natl. Acad. Sci. USA 89:1636–40.
Fisher et al., 1991, Neuron 6:371–380.
Flothe, et al., J. Biol. Chem., 268:3781–90 (1993).
Flotte, et al., Am. J. Respir. Cell. Mol. Biol., 7:349–56 (1992).
Flotte, et al., Proc. Nat. Acad. Sci. (USA), 90:10613–17 (1993).
Ho et al. (1988) Virology 167:279–83.
Horellou et al. (1994) Neuroreport 6:49–53.
Isacson, O. (1995) Science 269:856–7.
Jiao et al., 1993, Nature 362:450–53.
Kaplitt et al. (1991) Mol. Cellular Neurosciences 2:320–30.
Kaplitt et al. (1993) In: Current Top. Neuroendocrinol. vol. 11, pp. 169–91.
Kaplitt et al. (1994) Natur Genetics 8:148–53.
Klein et al., 1999, Neuroscience, 90:815–21.
Kremer et al. (1995) British Med. Bulletin 51:31–44.
Le Gal La Salle, G. Editorial, "Adventures with adenovirus", Nature Genetics 3:1–2 (1993).
Le Gal La Salle et al., "An adenovirus vector for gene transfer into neurons and glia in the brain", Science 259: 988–90 (1993), .
Lewis, R. (1995) Genetic Eng. News 15, No. 7: cover,17,25.
Mandel et al., 1999, Experimental Neurology 155:59–64.
Mandel et al., 1998, J. Neurosci. 18:4271–84.
McLaughlin et al. (1988) J. Virology 62:1963–73.
Muro–Cacho, et al., J. Immunother., 11:231–237 (1992).
Muzycka, N. (1994) J. Clin. Invest. 94:1351.
Muzyczka et al. Use of Adeno–associated Virus as a Mammalian Transduction Vector. pp. 39–44.
Muzyczka, 1992, Curr. Topics in Microbio. And Immu. 158:97–129.
Neve, "Adenovirus vectors enter the brain", TIBS, 16:251–253 (1993).
Ohi et al. (1990) Gene 89:279–82.
Orkin et al., Dec. 7, 1995, Orkin et al., NIH Gene Therapy Meeting Report.
Palella et al. (1988) Mol. Cell. Biol. 457–60.
Palella et al. (1989) Gene 80:137–44.
Roessler et al. (1994) Neurosci. Lett. 167:5–10.
Samulski, Curr. Op. Gen. Devel., 3:74–80 (1993).
Samulski et al. (1991) EMBO J. 10:3941–50.
Samulski et al., J. Virol., 63:3822–28 (1989)

(List continued on next page.)

*Primary Examiner*—James Martinell
(74) *Attorney, Agent, or Firm*—Klauber & Jackson

(57) ABSTRACT

The invention relates to a method of delivering exogenous DNA to a target cell of the mammalian central nervous system using an adeno-associated virus (AAV)-derived vector. Also included in the invention are the AAV-derived vectors containing exogenous DNA which encodes a protein or proteins which prevent or treat nervous system disease, and a method of prevent or treating such disease.

26 Claims, 6 Drawing Sheets

OTHER PUBLICATIONS

Samulski et al., J. Virol., 61:3096–101 (1987).
Spaete et al. (1982) Cell 30:295–304.
Srivastava, A. (1994) Blood Cells 20:531–8.
Szczypka et al., 1999, Neuron 22: 167–78.
Tenenbaum et al., Meeting on Gene Transfor into Neurones, Abstract, Aug. 16–18, 1993.
Walsh, et al., Proc. Nal. Acad. Sci. (USA), 89:7257–61 (1992).
Wolff et al., 1989, PNAS USA 86:9011–14.
Wolff (1993) *Curr. Opin.Neurobiol.*3:743–748.
Wu et al. (1994) Mol. Brain Res. 24:27–33.
Wu et al., 1993, Society for Neuroscience Abs. 19:391.
Xiao et al., 1993, Advanced Drug Reviews 12:201–215.

* cited by examiner

AAV-MEDIATED DELIVERY OF DNA TO CELLS OF THE NERVOUS SYSTEM

RELATED APPLICATION

This is application is a continuation of application U.S. Ser. No. 08/467,044, filed Jun. 6, 1995, U.S. Pat. No. 6,180,613 which is hereby incorporated by reference in its entirety, which is a continuation-in-part of copending application U.S. Ser. No. 08/227,319 filed on Apr. 13, 1994 now abandoned. Applicants claim the benefit of both of these applications under 35 U.S.C. §120.

BACKGROUND OF THE INVENTION

1. Field of the Invention

The present invention relates to the delivery of DNA to and the expression of delivered genes in, cells of the nervous system.

2. Description of the Related Art

The first human gene therapy trial started in September 1990 and involved retrovirally-mediated transfer of the adenosine deaminase (ADA) gene into lymphocytes of patients with severe combined immunodeficiency (SCID). The, favorable results of this trial stimulated further interest in gene therapy resulting in further 67 gene therapy clinical protocols approved by the NIH Recombinant DNA Advisory Committee (RAC) to date. Although the original promise of gene therapy was the development of a curative treatment for simple, single gene diseases, the vast majority of gene therapy trials have been for complex genetic or acquired diseases, such as infectious disease and cancer. A large number of the initial clinical gene transfer studies were not gene therapy but rather gene marking studies. The first type of marking experiments used tumor infiltrating lymphocytes which were transduced in vitro with retroviral vectors prior to infusion into patients with cancer. The second class of gene marking studies involved the attempt to detect residual tumor cells in marrow infused into patients following ablative chemotherapy.

Of the currently approved gene therapy trials, all trials prior to 1992 used retroviral vectors and the diseases targeted included SCID, familial hypercholesteremia and cancer. More recently, gene therapy trials have commenced for AIDS and Hemophilia B, again using retroviral vectors. In addition, adenoviral vectors have recently been approved for cystic fibrosis. The vast majority of these protocols have enrolled very few patients at present and most of the trials are as yet unpublished. The available data however appears promising, for example the expression of the LDL receptor in the liver following ex vivo transduction of resected hepatocytes and its infusion into the portal vein in patients with familial hypercholesteremia has resulted in a 20% drop in plasma cholesterol levels (Randall (1992) JAMA 269:837–838). It is likely therefore that there will be an exponential growth in gene therapy trials and a large number of medical schools and teaching hospitals are setting up gene therapy centers.

The ability to deliver genes to the nervous system, and to manipulate their expression, may make possible the treatment of numerous neurological disorders. Unfortunately, gene transfer into the central nervous system (CNS) presents several problems including the relative inaccessibility of the brain and the blood-brain-barrier, and that neurons of the postnatal brain are post-mitotic. The standard approach for somatic cell gene transfer, i.e., that of retroviral vectors, is not feasible for the brain, as retrovirally mediated gene transfer requires at least one cell division for integration and expression. A number of new vectors and non-viral methods have therefore been used for gene transfer in the CNS. Although the first studies of gene transfer in the CNS used an ex vivo approach, i.e., the transplantation of retrovirally-transduced cells, more recently several groups have also used an in vivo approach. Investigators have used HSV-1 and adenoviral vectors as well as non-viral methods including cationic lipid mediated transfection (Wolff (1993) Curr. Opin. Biol. 3:743–748).

The ex vivo approach is illustrated by a recent study in which oligodendrocytes were retrovirally infected and transplanted into a syngeneic rat model for demyelination (Groves et al (1993) Nature 362:453–457). In addition to the use of brain cells as vehicles for foreign gene expression in the CNS, non-neuronal cells including fibroblasts and primary muscle cells have also been used (Horrelou et al (1990) Neuron 5:393–402; Jiao et al (1993) Nature 362:450–453).

The in vivo approach was initially largely based on the use of the neurotropic Herpes Simplex Virus (HSV-1), however, HSV vectors present several problems, including instability of expression and reversion to wild-type (see below). A more recent development has been the use of adenoviral vectors. Adenoviral vector studies have shown expression of marker genes into the rat brain persisting for two months although expression fell off dramatically (Davidson et al (1993) Nature Genetics 3:219–2223). In addition to viral vector approaches, other investigators have used direct injection of a cationic liposome:plasmid complex obtaining low level and transient expression of a marker gene (Ono et al (1990) Neurosci. Lett. 117:259–263).

There have been very few studies using "therapeutic" genes in the CNS. The majority of these have used the ex vivo approach with transduction of fibroblasts and muscle cells with the human tyrosine hydroxylase gene in order to produce L-dopa-secreting cells for use in models of Parkinson's Disease (e.g., Horrelou et al (1990) Neuron 5:393–402; Jiao et al (1993) Nature 362:450–453). Of the in vivo approaches, HSV vectors have been used to express β-glucuronidase (Wolfe et al (1992) Nature Genetics 1:379–384), glucose transporter (Ho et al (1993) Proc. Natl. Acad. Sci. 90:6791–6795) and nerve growth factor (Federoff et al (1992) Proc. Natl. Acad. Sci. 89:1636–1640). An adenoviral vector has been used to induce low level transient expression of human α1-antitrypsin (Bajoccchi et al (1993) 3:229–234).

The only clinical studies of gene transfer in the brain followed a report by Culver et al (1992) Science 256:18550–18522) in which they essentially cured rats which had been intracerebrally implanted with glioma cell lines. They used a retrovirus expressing the HSV-1 thymidine kinase (tk) gene and then subsequently treated with ganciclovir. In 1993, a human protocol for glioblastoma multiforme was approved using the retroviral tk vector—ganciclovir protocol (Oldfield et al (1993) Human Gene Ther. 4:39–69).

Herpes Viruses The genome of the herpes simplex virus type-1 (HSV-1) is about 150 kb of linear, double-stranded DNA, featuring about 70 genes. Many viral genes may be deleted without the virus losing its ability to propagate. The "immediately early" (IE) genes are transcribed first. They encode trans-acting factors which regulate expression of other viral genes. The "early" (E) gene products participate in replication of viral DNA. The late genes encode the structural components of the virion as well as proteins which turns on transcription of the IE and E genes or disrupt host cell protein translation.

After viral entry into the nucleus of a neuron, the viral DNA can enter a state of latency, existing as circular episomal elements in the nucleus. While in the latent state, its transcriptional activity is reduced. If the virus does not enter latency, or if it is reactivated, the virus produces numerous infectious particles, which leads rapidly to the death of the neuron. HSV-1 is efficiently transported between synaptically connected neurons, and hence can spread rapidly through the nervous system.

Two types of HSV vectors have been utilized for gene transfer into the nervous system. Recombinant HSV vectors involve the removal of an immediate-early gene within the HSV genome (ICP4, for example), and replacement with the gene of interest. Although removal of this gene prevents replication and spread of the virus within cells which do not complement for the missing HSV protein, all of the other genes within the HSV genome are retained. Replication and spread of such viruses in vivo is thereby limited, but expression of viral genes within infected cells continues. Several of the viral expression products may be directly toxic to the recipient cell, and expression of viral genes within cells expressing MHC antigens can induce harmful immune reactions. In addition, nearly all adults harbor latent herpes simplex viruses within neurons, and the presence of recombinant HSV vectors could result in recombinations which can produce an actively replicating wild-type virus. Alternatively, expression of viral genes from the recombinant vector within a cell harboring a latent virus might promote reactivation of the virus. Finally, long-term expression from the recombinant HSV vector has not been reliably demonstrated. It is likely that, except for conditions in which latency is induced, the inability of HSV genomes to integrate within host DNA results in susceptibility to degradation of the vector DNA.

In an attempt to circumvent the difficulties inherent in the recombinant HSV vector, defective HSV vectors were employed as gene transfer vehicles within the nervous system. The defective HSV vector is a plasmid-based system, whereby a plasmid vector (termed an amplicon) is generated which contains the gene of interest and two cis-acting HSV recognition signals. These are the origin of DNA replication and the cleavage packaging signal. These sequences encode no HSV gene products. In the presence of HSV proteins provided by a helper virus, the amplicon is replicated and packaged into an HSV coat. This vector therefore expresses no viral gene products within the recipient cell, and recombination with or reactivation of latent viruses by the vector is limited due to the minimal amount of HSV DNA sequence present within the defective HSV vector genome. The major limitation of this system, however, is the inability to eliminate residual helper virus from the defective vector stock. The helper virus is often a mutant HSV which, like the recombinant vectors, can only replicate under permissive conditions in tissue culture. The continued presence of mutant helper HSV within the defective vector stock, however, presents problems which are similar to those enumerated above in regard to the recombinant HSV vector. This would therefore serve to limit the usefulness of the defective HSV vector for human applications.

For further information on HSV-mediated gene delivery to neurons, see Breakefield and DeLuca, "Herpes Simplex Virus for Gene Delivery to Neurons," (1991) *New Biologist* 3:203–18; Ho and Mocarski (1988) "Beta-Galactosidase as a marker in the herpes simplex virus-infected mouse," *Virology* 167:279–93; Palella, et al (1988) "Herpes Simplex Virus-Mediated human hypoxanthine-guanine phosphoribosyl-transferase gene transfer into neuronal cells," *Molec. & Cell. Biol.* 8:457–60; Pallela et al (1988) "Expression of human HPRT mRNA in brains of mice infected with a recombinant herpes simplex virus-1 vector," *Gene* 80:137–144; Andersen et al (1992) "Gene transfer into mammalian central nervous system using the neuron-specific enolase promoter," *Human Gene Therapy* 3:487–99; Kaplitt et al (1993) "Molecular alterations in nerve cells: Direct manipulation and physiological mediation," *Curr. Topics Neuroendocrinol.* 11:169–191; Spaele and Frenkel (1982) "The Herpes Simplex Virus Amplicon: A New Eukaryotic Defective-Virus-Cloning-Amplifying Vector," *Cell* 30:295–304 (1982); Kaplitt et al (1991) "Expression of a Functional Foreign Gene in Adult Mammalian Brain Following In Vivo Tranfers via a Herpes-Simplex Virus. Type 1 Detective Viral Vector," *Molec. & Cell. Neurosci.* 2:320–30; Federoff et al (1992) "Expression of Nerve Growth Factor In Vivo form a Defective Herpes Simplex Virus 1 Vector Prevents Effects of Axotomy on Sympathetic Ganglia," *Proc. Nat. Acad. Sci. (USA)* 89:1636–40.

While HSV vectors of reduced toxicity and replication ability have been suggested, they can still mutate to a more dangerous form, or activate a latent virus, and, since the HSV does not integrate, achieving long-term expression would be difficult.

Adenoviruses

The adenovirus genome consists of about 36 kb of double-stranded DNA. Adenoviruses target airway epithelial cells, but are capable of infecting neural cells.

Recombinant adenovirus vectors have been used as gene transfer vehicles for non-dividing cells. These vectors are similar to recombinant HSV vectors, since the adenovirus E1a immediate-early gene is removed but most viral genes are retained. Since the E1a gene is small (roughly 1.5 kb) and the adenovirus genome is ⅓ the size of the HSV genome, other non-essential adenovirus are removed in order to insert a foreign gene within the adenovirus genome.

In nature, diseases resulting from adenovirus infections are not as severe as those induced by HSV infection, and this is the principal advantage of recombinant adenovirus vectors compared with HSV vectors. However, retention and expression of many adenovirus genes presents problems similar to those described with the HSV vector, particularly the problem of cytotoxicity to the recipient cell. In addition, recombinant adenovirus vectors often elicit immune responses which may serve to both limit the effectiveness of vector-mediated gene transfer and may provide another means for destruction of transduced cells. Finally, as with the HSV vectors, stability of long-term expression is currently unclear since there is no mechanism for specific viral integration in the genome of non-dividing host cells at high frequency. While theoretically possible, defective adenovirus vectors would be difficult to make as at least 20% of the Ad genome is required for packaging (about 27 kb) and vectors this size are difficult to work with. In contrast, the defective HSV vectors are small plasmids which replicate until the correct aggregate size is reached for proper packaging.

For more information on vectors, see Akli et al (1993) "Transfer of a foreign gene into the brain using adenovirus vectors," *Nature Genetics* 3:224–228; La Salle, et al, "An adenovirus vector for gene transfer into neurons and glia in the brain," *Science* 259:988–90 (1993), Editorial, "Adventures with adenovirus," 3:1–2 (1993); Neve, "Adenovirus vectors enter the brain" *TIBS* 16:251–253 (1993).

Adeno-Associated Virus is a defective parvovirus whose genome is encapsidated as a single-stranded DNA molecule.

Strands of plus and minus polarity are both packaged, but in separate virus particles. Although AAV can replicate under special circumstances in the absence of a helper virus, efficient replication requires coinfection with a helper virus of the herpesvirus or adenovirus family. In the absence of the helper virus, AAV establishes a latent infection in which the viral genome exists as an integrated provirus in the host cell. (No AAV gene expression is required to establish a latent infection). The integration of the virus is site-specific (chromosome 19). If a latently infected cell line is later superinfected with a suitable helper virus, the AAV provirus is excised and the virus enters the "productive" phase of its life cycle. However, it has been reported that certain AAV-derived transducing vectors are not rescued by adenovirus superinfection.

Although AAV is a human virus, its host range for lytic growth is unusually broad. Cell lines from virtually every mammalian species tested (including a variety of human, simian, canine, bovine and rodent cell lines) can be productively infected with AAV, provided an appropriate helper virus is used (e.g., canine adenovirus in canine cells). Despite this, no disease has been associated with AAV in either human or other animal populations, unlike both HSV and adenovirus.

AAV has been isolated as a nonpathogenic coinfecting agent from fecal, ocular and respiratory specimens during acute adenovirus infections, but not during other illnesses.

Likewise, latent AAV infections have been identified in both human and nonhuman cells. Overall, virus integration appears to have no apparent effect on cell growth or morphology. See Samulski (1993) *Curr. Op. Gen. Devel.* 3:74–80.

The genome of AAV-2 is 4,675 bases in length and is flanked by inverted terminal repeat sequences of 145 bases each. These repeats are believed to act as origins for DNA replication.

There are two major open reading frames. The left frame encodes at least four non-structural proteins (the Rep group). There are two promoters P5 and P19, which control expression of these proteins. As a result of differential splicing, the P5 promoter directs production of proteins Rep 78 and Rep 68, and the P19 promoter, Rep 52 and Rep 40. The Rep proteins are believed to be involved in viral DNA replication, trans-activation of transcription from the viral promoters, and repression of heterologous enhancers and promoters.

The right ORF, controlled by the P40 promoter, encodes the capsid proteins Vp1 (91 kDa), Vp2 (72 kDa) and Vp3 (60 kDa). Vp3 comprises 80% of the virion structure, while Vp1 and Vp2 are minor components. There is a polyadenylation site at map unit 95. For the complete sequence of the AAV-2 genome, see Vastava et al (1983) *J. Virol.* 45:555–64.

McLaughlin et al ((1988) *J. Virol.* 62:1963–73) prepared two AAV vectors: dl 52–91, which retains the AAV rep genes, and dl 3–94, in which all of the AAV coding sequences have been deleted. It does, however, retain the two 145 base terminal repeats, and an additional 139 bases which contain the AAV polyadenylation signal. Restriction sites were introduced on either side of the signal.

A foreign gene, encoding neomycin resistance, was inserted into both vectors. Viral stocks were prepared by complementation with a recombinant AAV genome, which supplied the missing AAV gene products in trans but was itself too large to be packaged.

Unfortunately, the virus stocks were contaminated with wild type AAV (10% in the case of dl 3–94) presumably as a result of homologous recombination between the defective and the complementing virus.

Samulski et al ((1989) *J. Virol.* 63:3822–28) developed a method of producing recombinant AAV stocks without detectable wild-type helper AAV. Their AAV vector retained only the terminal 191 bases of the AAV chromosome. In the helper AAV, the terminal 191 bases of the AAV chromosome were replaced with adenovirus terminal sequences. Since sequence homology between the vector and the helper AAV was thus essentially eliminated, no detectable wild-type AAV was generated by homologous recombination. Moreover, the helper DNA itself was not replicated and encapsidated because the AAV termini are required for this process. Thus, in the AAV system, unlike the HSV system, helper virus could be completely eliminated leaving a helper-free AAV vector stock.

Muro-Cacho et al ((1992) *J. Immunother.* 11:231–237) have used AAV-based vectors for gene transfer into both T- and B-lymphocytes. Walsh et al ((1992) *Proc. Nat. Acad. Sci. (USA)* 89:7257–61) used an AAV vector to introduce a human gamma globulin gene into human erythroleukemia cells; the gene was expressed. Flothe et al ((1993) *J. Biol. Chem.* 268:3781–90) delivered the cystic fibrosis transmembrane conductance regulator gene to airway epithelial cells by means of an AAV vector. See also Flotte et al (1992) *Am. J. Respir. Cell. Mol. Biol.* 7:349–56; Flotte et al (1993) *Proc. Nat. Acad. Sci. (USA)* 90:10613–17.

SUMMARY OF THE INVENTION

Adeno-associated virus has not been reported to naturally infect any nervous system cells, and AAV-derived vectors have not previously been used to transfect terminally differentiated, non-dividing cells. Nonetheless, the present invention demonstrates that an adeno-associated virus-derived vector may be used to deliver exogenous DNA to cells of the postnatal central and/or peripheral nervous system, including neurons and glia, even though these cells are non-dividing. Specificity may be achieved by anatomically specific delivery or by tissue specific expression.

The exogenous DNA preferably comprises a gene which encodes a gene product useful in the treatment of a nervous system disorder. This gene, in some embodiments, is operably linked to a promoter specific for particular cell types or regions within the nervous system. Because the AAV vector is integrated, stable, longterm expression (e.g., for greater than seven months) can be achieved.

DETAILED DESCRIPTION OF THE PREFERRED EMBODIMENTS

The Vector

Figure 1:
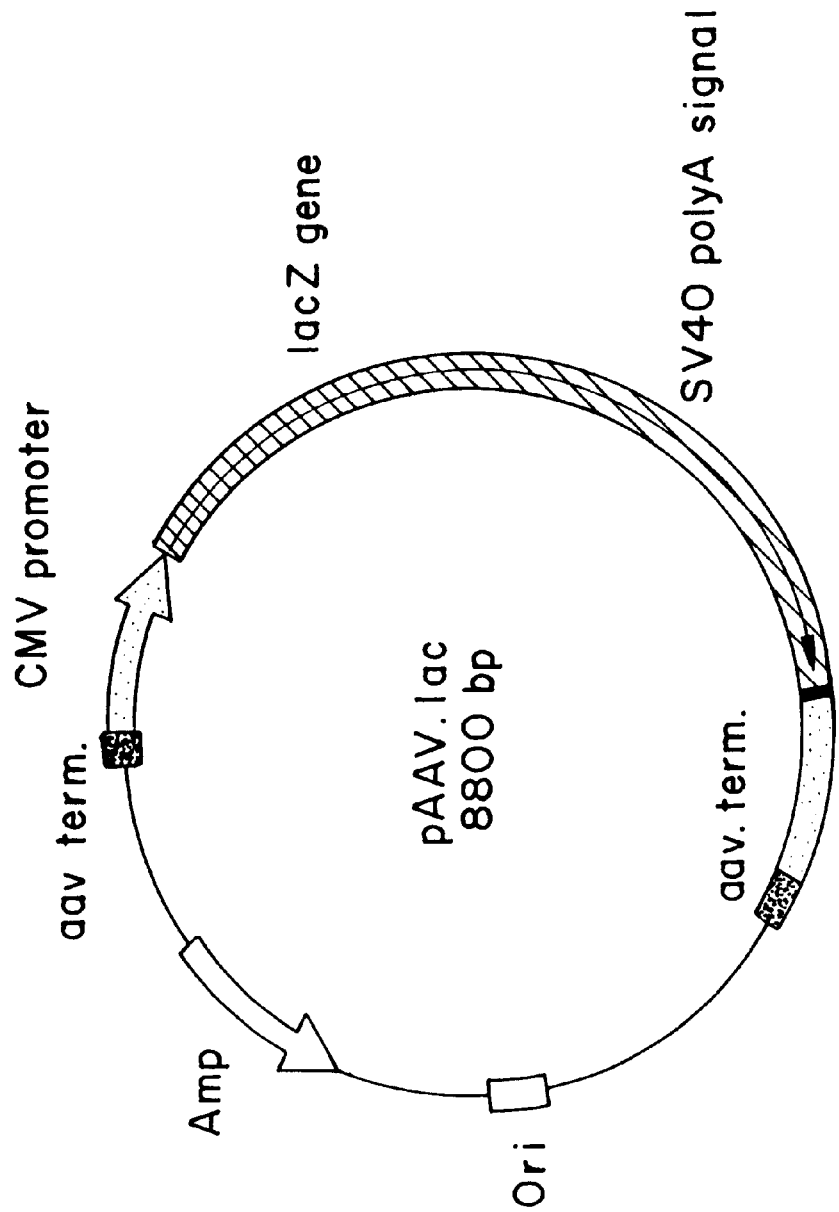
FIG. 1 is a map of the AAV vector pAAVlac.

The vector of the present invention is a derivative of the adeno-associated virus, into which exogenous DNA has been introduced.

While the wild-type adeno-associated virus is already defective, in that it requires the presence of a helper virus for lytic infection, there is the possibility that the subject to whom the vector is delivered will harbor a herpesvirus or adenovirus infection which can complement the vector. To guard against this possibility, it is highly preferred that the vector be modified to reduce the possibility of rescue. In theory, such modifications can take the form of point mutations to one or more viral genes, which mutations either prevent expression of the gene altogether, or result in the expression of a modified gene product which is nonfunctional. However, point mutations are reversible. Consequently, it is preferable that each undesired gene simply be deleted, which has the additional advantage of creating more room within the viral package for foreign DNA.

It is preferable that all of the viral genes be deleted, or otherwise inactivated, as in the known AAV vector dl3–94. However, it should be understood that a vector retaining one or more AAV genes such as the known AAV vector dl52–91, may still be useful for gene delivery, although inferior to the preferred vectors.

For propagation of the vector in vitro, susceptible cells are co-transfected with the AAV-derived vector and a suitable AAV-derived helper virus or plasmid. Preferably, the vector retains from AAV essentially only the recognition signals for replication and packaging.

It is not necessary that the AAV-derived sequences correspond exactly with their wild-type prototypes. For example, the AAV vectors of the present invention may feature mutated inverted terminal repeats, etc., provided that the vector can still be replicated and packaged with the assistance of helper virus, and still establish a nonpathogenic latent infection in target cells.

The vector may further comprise one or more restriction sites into which foreign DNA may be cloned without interfering with packaging and replication. Preferably, at least one unique restriction site is provided. The vector may also comprise one or more marker genes to facilitate genetic manipulation. Suitable marker genes include, but are not limited to, the neomycin and hygromycin resistance genes, bacterial lacZ, and the firefly luciferase gene.

The AAV-derived Helper Virus or Plasmid

The AAV-derived helper virus or plasmid may be any virus or plasmid which is capable, upon expression of the carried AAV genes, of providing proteins necessary for the replication and packaging of the vector in vitro in a suitable host cell, for the purpose of producing vector stock.

In a preferred embodiment, the helper virus or plasmid is one which has been engineered to reduce the risk of recombination between the helper DNA and the vector DNA. Most desirably, there is essentially no sequence homology between the AAV sequences of the vector DNA, and the AAV sequences of the helper DNA. For example, the helper DNA may be an AAV in which the AAV inverted terminal repeats are replaced by the corresponding sequences of another virus, such as adenovirus (e.g., adenovirus type 5 DNA). See Samulski et al *J. Virol.* 63:3822–28.

Alternatively, in another preferred embodiment, helper adenovirus may be removed by heat inactivation at 56° C. for 30 minutes, or separated from packaged AAV vectors by centrifugation in a cesium chloride gradient.

Exogenous DNA

Basic procedures for constructing recombinant DNA and RNA molecules in accordance with the present invention are disclosed by Sambrook, J. et al, In: *Molecular Cloning: A Laboratory Manual*, Second Edition, Cold Spring Harbor Press, Cold Spring Harbor, N.Y. (1989), which reference is herein incorporated by reference.

The "exogenous DNA" of the present invention should be exogenous to both AAV and to the target cell. The DNA may be synthetic DNA, complementary DNA, genomic DNA, or a combination thereof. The DNA may be of any sequence or length, provided that it may be incorporated into the vector and delivered to target cells. Typically, because of the packaging limitations of AAV, the exogenous DNA will have a length of about 10–5,000 bases. Preferably, the DNA is 100 to 4,000 bases.

The present invention may be used for gene therapy of any genetically-based or -acquired nervous system disorder. An individual may be in need of gene therapy because, as a result of one or more mutations in the regulatory region and/or the coding sequence of one or more genes, a particular gene product is inappropriately expressed, e.g., has an incorrect amino acid sequence, or is expressed in the wrong tissues or at the wrong times, is underexpressed or overexpressed. Therefore, DNA delivered to that individual may be considered exogenous even though it is identical to a gene native to that individual's species, provided it differs in the regulatory or coding region from the cognate gene of the individual to whom it is delivered, and therefore encodes a different gene product or is expressed to a different degree and/or in different cells, under at least some conditions.

Parkinson's Disease

Current approaches to Parkinson's Disease (PD) are based on facilitating dopaminergic neurotransmission in the caudate-putamen (CP). The mainstay of treatment is oral L-Dopa (and a peripheral decarboxylase inhibitor), which is converted to dopamine by endogenous AADC in the denervated CP. Alternative pharmacological approaches include direct dopamine agonists including bromocriptine and apomorphine, as well as dopamine metabolizing enzyme (e.g. monoamine oxidase) inhibitors (MAOI), e.g. deprenyl. Although these treatments have made a significant improvement in the short term quality of life of PD patients, the disease progresses with all patients ultimately becoming refractory to oral treatment over 5 to 10 years.

Alternative investigative strategies have included fetal and adrenal transplantation, which although showing promise in animal models of PD, have had marginal efficacy in the human. Moreover, these transplantation approaches disturb the neuronal environment, abnormal sprouting and synapse formation occurs and the transplanted cells may induce an immune response as well as being targeted for the same underlying neurodegeneration responsible for the PD. A further implantation strategy includes a polymer or encapsulation device in which cells either dopamine-producing (e.g. PC 12) or genetically engineered cells (fibroblasts or neuronal cell lines which have been transduced, typically by retroviruses, to express tyrosine hydroxylase enzyme [THE]). These implants also disturb the neuronal circuitry, create significant injury in view of the size of the implant and moreover generate high local concentrations of dopamine to potentially toxic concentrations.

A more elegant approach is to use a viral vector to transduce neurons in vivo. We have previously established that an HSV-1 vector expressing THE can be stereotactically implanted into the denervated striatum of a rat model of PD and obtain biochemical and behavioral recovery extending at least one year (During et al, submitted).

The current invention has the significant advantages over the HSV-1 defective vector approach. Specifically, the reversion frequency of the defective HSV-1 virus is approximately $10^{-5}$, and with the amounts of virus needed for in vivo studies sufficient wild type herpes infection occurs to result in toxicity and the death of experimental animals. Furthermore, although expression in the first two weeks is high, the level of vector gene expression beyond 2 weeks is reduced, perhaps to 5–20% of the initial expression.

The current invention also provides a major advantage over approaches which limit expression to THE. In PD (and the denervated striatum in animal models of PD) not only is the enzyme THE decreased by 80–100%, but the second enzyme in the dopamine biosynthetic pathway, AADC, is also decreased by approximately 85%. As L-Dopa per se does not restore dopaminergic activity and behavioral recovery in PD, production of dopamine in the denervated striatum where THE is restored may become limited by the activity of AADC. The ability for cells to acquire the full dopaminergic phenotype (by expressing both THE and AADC) is likely to be more effective. In support of this claim, one group has shown that when comparing animals transplanted with genetically engineered cells expressing only THE to animals implanted with both THE and AADC expressing transplants, the latter group had better recovery.

Therefore, in one embodiment, the vectors of the present invention are used to deliver the gene for tyrosine hydroxylase (Genbank HUMTHX, Accession No. M17589) to brain cells. Preferably, the gene for aromatic amino-acid decarboxylase (Genbank HUMDDC, Accession No. M76180) is similarly delivered, by the same or a separate vector.

The above description of transducing striatal cells in vivo to a dopaminergic phenotype is the first step in a gene therapy approach to PD. However, PD becomes symptomatic when 80% of the dopamine neurons have been lost. Degeneration is progressive and with further denervation patients become increasingly refractory to all current therapies and exhibit "On-Off" phenomenon with increasing freezing and complete immobility. Transducing striatal cells with a viral vector to express dopamine synthesizing enzymes is purely a palliative approach and the underlying disease process will continue unabated. To this end vectors have been constructed expressing "neuroprotective or neurotrophic" factors to prevent further degeneration of dopaminergic neurons and promote regeneration. This approach includes the most specific neurotrophic factor for mesencephalic dopaminergic neurons identified to date, glial-derived neurotrophic factor (GDNF). Other neurotrophic factors of the NGF family have previously been expressed from HSV-1 vectors and shown to have neuroprotective effects (Federoff et al). These neurotrophic factors appear to act through tyrosine kinase receptors to prevent apoptosis or programmed cell death (PCD). As the proto-oncogene bcl-2 can prevent neuronal PCD in vitro, an AAV vector has been constructed expressing bcl-2 to prevent PCD in vivo. This vector might therefore be considered for any neuronal degeneration in the brain including ischemia, epilepsy or brain trauma where secondary neuronal injury occurs via PCD.

Therefore, gene therapy for PD could involve delivery, by AAV vectors, of the gene for GDNF (Genbank HUMGDNF02; Accession No. L19063), brain-derived neurotrophic factor (BDNF), nerve growth factor (NGF) (EMBL HSNGF2; Accession No. X53655, and/or other members of the neurotrophin factor family including neurotrophin (NT)-3 (Genbank HUMBDNF; Accession No. M37762) and NT-4 (Genbank HUMPPNT4P; Accession No. M86528).

Recent evidence strongly implicates oxidative stress in the substantia nigra as a primary determinant of the progressive neuronal loss. Specifically, iron appears to be concentrated in the nigra of PD patients and studies have shown iron binding to neuromelanin of the nigra cells to generate free radicals. An antioxidant strategy to PD has therefore been proposed. The key enzymes which reduce free radical generation and/or scavenge free radicals are superoxide dismutase (SOD), catalase and glutathione peroxidase (GPO). Although mutations or alterations in expression of these enzymes has not yet been determined in PD, the increased expression of these enzymes in the nigrostriatal dopaminergic neurons will increase their ability to withstand oxidative stress. Therefore, an AAV vector has been made expressing SOD. This SOD expressing vector is also of interest in the treatment of amyotrophic lateral sclerosis (ALS) in which in the familial form is associated with mutations in the SOD-1 gene.

Therefore, it may be desirable to use AAV vectors to deliver the genes for superoxide dismutase (SOD1 or SOD2) (GenBank HUMCUZNDI; Accession No. M12367; for SOD-1, EMBL HSSOD2G, Accession No. X65965 for SOD-2), catalase (EMBL HSCATR, Accession No. X04076), and/or glutathione peroxidase (MBL HSGSHPX, Accession No. Y00433).

Epilepsy

Complex partial seizures and specifically temporal lobe epilepsy (TLE) is one of the most refractory forms of epilepsy. Although antiepileptic drugs (AED) will control seizures in some patients, 40% will remain uncontrolled despite polyAED therapy. The current approach for these patients is to undergo a phased evaluation for consideration of resective surgery. Typically, one temporal lobe is defined as the site of seizure origin (the epileptogenic region) and the medial temporal lobe including the anterior hippocampus is resected. TLE is not a genetic disease and there is no established aetiology, however the disease results from an imbalance of excitation to inhibition with interventions enhancing excitation or blocking inhibition producing seizures and conversely the antagonism of excitation and enhancing of inhibition has an antiepileptic effect. One gene therapy approach to TLE is to improve inhibition. To this end, the adenosine A-1 receptor (GenBank S56143; Accession S56143) cDNA has been inserted into the AAV vector. As adenosine has been shown to be the brain's natural anticonvulsant (acting through A-1 receptors) and levels of the receptor are decreased in the epileptogenic region, this strategy is likely to enhance inhibition and prevent seizures.

Alternative strategies to increase inhibition include the insertion of genes whose expression would enhance GABAergic activity. These genes would include $GABA_A$ receptor isoforms and the GABA synthesizing enzyme, GAD.

One related approach to increase inhibition is to increase expression of ion channels which alter neuronal excitability, specifically activity dependent channels including calcium-activated potassium channels and ATP-sensitive potassium channels.

A complementary approach is to express an antisense to excitatory receptors specifically glutamate receptors including NMDAR's, mGluR's and ionotropic glutamate receptors including both AMPA and kainate. As we have shown that expression of GluR6 using a HSV-1 vector induces epilepsy, it is reasonable to predict that a vector expressing antisense to these receptor types may inhibit seizures.

Therefore, for the treatment of epilepsy, genes encoding adenosine A-1 receptor (GenBank S56143; Accession S56143, glutamate decarboxylase (GenBank S61898; Accession S61898), GABA-A receptor isoforms (EMBL HSGABAAA1; Accession X14766), calcium-dependent potassium channels (GenBank DROKCHAN, Accession M96840) and/or ATP-sensitive potassium channels (Ho, et al 1993 *Nature* 362:31–8) may be delivered by AAV vectors.

Brain Tumors

Brain tumors are intractable and usually lethal diseases which largely affect children and adults in middle age. Currently, there are no known causes of most brain tumors and treatment modalities have been largely ineffectual. There have been two recent strategies using gene therapy as possible approaches for brain tumor therapy. In the first approach, a mutant HSV has been used which can replicate only in dividing cells. This should result in destruction of dividing tumor cells while sparing non-dividing cells in the healthy brain. Although there has been some experimental evidence supporting the fact that these viruses do reduce the rate of brain tumor growth in experimental animals, results have been variable and not as impressive as would be desired. There have been no human trials of this method.

The second approach involves the insertion of the thymidine kinase (TK) gene from herpes simplex virus type 1 into a replication-deficient retroviral vector. The retroviral vector only transferred the TK gene into dividing tumor cells, but could not transfer genes either into non-dividing tumor cells or healthy brain tissue.

It was found in tissue culture and in animal tumors that cells transduced with TK via the retroviral vector would become susceptible to cytotoxicity by the drug ganciclovir. TK phosphorylates ganciclovir, and the phosphorylated form disrupts DNA replication and thereby kills dividing cells. It was also found that nearby dividing cells which were not transduced with TK could also be killed. This was called the bystander effect, as it is believed that some phosphorylated drug can exit the transduced cell and enter nearby, non-transduced cells via gap junctions. Non-dividing cells are unaffected even by activated drug. This approach to tumor therapy is currently in clinical trials at the NIH.

Since results with this therapy have also been variable in animal studies, more recent experiments have shown that use of a replication-competent retroviral vector can improve the response in animals. This approach would not be applicable to human disease, however, due to the extreme danger of placing large amounts of wild-type retroviruses directly into human patients. This has never been permitted in human patients previously due to the potential for cytotoxicity and induction of de novo tumors following random integration of wild-type retroviruses into the genome of the recipient cell.

This embodiment of the current invention envisions a significant improvement over these previous studies. Insertion of the TK gene (EMBL HEHSV1TK, Accession X03764; EMBL HEHS07, Accession V00466), into the AAV vector should permit transduction of genes into dividing tumor cells with efficiencies that are at least equal to retroviral vectors, and possibly with greater efficiency (which has been observed in comparisons of AAV and defective HSV vectors in rat brain). Unlike retroviruses, however, AAV vectors will also transfer the TK gene into slowly dividing or non-dividing cells within tumors as well as non-dividing normal cells. This could have two significant advantages compared with retroviral vectors.

First, the ability to phosphorylate drugs within non-dividing tumor cells and normal cells should create a greater pool of activated drug within the tumor. Given the observation of the bystander effect, non-dividing tumor cells containing the HSV TK gene should phosphorylate the drug and this could then enter a nearby dividing cell which may not have been transduced with the viral gene. Thus, a non-dividing cell could permit destruction of a nearby, non-transduced cell, even though the transduced, non-dividing cell would not be adversely effected. In this manner, a greater population of dividing cells would be destroyed.

The second advantage is the ability of AAV vectors to integrate in non-dividing cells. If a retrovirus enters a non-dividing cell, reverse transcription does not occur and the vector is lost. When the AAV vector enters a non-dividing tumor cell, however, the vector should integrate into the host genome. Thus, if that tumor cell then re-enters cell division, the TK gene should be retained in that cell and all progeny. This should then render such previously quiescent tumor cells susceptible to destruction by ganciclovir or an analog. Since retroviral vectors are lost in non-dividing cells, and other DNA viral vectors do not reliably integrate within the host genome, the ability to retain the TK gene if a quiescent cell begins division is a property unique to the AAV vector. Finally, it should be reiterated that integration of the AAV vector should not result in disruption or abnormal regulation of host genes, and that transduction of normal non-dividing cells with TK should not have any adverse effects, since it is the subsequent activation of the drug by TK which blocks DNA replication and this only results in destruction of dividing cells. Thus, this embodiment of the invention provides substantial improvements over previous drug-susceptibility tumor treatment strategies.

Target Cells

The target cells of the vectors of the present invention are cells of the central or peripheral nervous systems of a mammal. In one embodiment, the cells are cells cultured in vitro.

In another embodiment, the cells are part of a living mammal at the time the vector is delivered of the cell. The mammal may be at any stage of development at the time of delivery, e.g., embryonic, fetal, infantile, juvenile or adult.

The vector may be delivered to cells of the central nervous system, cells of the peripheral nervous system, or both. When the vector is delivered to the cells of the central nervous system, it may be delivered to cells of the spinal cord, brainstem (medulla, pons, and midbrain), cerebellum, diencephalon (thalamus, hypothalamus), telencephalon (corpus striatum, cerebral cortex, or, within the cortex, the occipital, temporal, parietal or frontal lobes), or combinations thereof.

Similarly, within the peripheral nervous system, it may be delivered to cells of the sensory and/or effector pathways.

To deliver the vector specifically to a particular region of the central nervous system, it may be administered by stereotaxic microinjection, as exemplified in Example 2. For example, on the day of surgery, patients will have the stereotactic frame base fixed in place (screwed into the skull). The brain with stereotactic frame base (MRI-compatible with fiducial markings) will be imaged using high resolution MRI. The MRI images will then be transferred to a computer which runs stereotactic software. A series of coronal, sagittal and axial images will be used to determine the target (site of AAV vector injection) and trajectory. The software directly translates the trajectory into 3 dimensional coordinates appropriate for the stereotactic frame. Burr holes are drilled above the entry site and the stereotactic apparatus positioned with the needle implanted at the given depth. The AAV vector will then be injected at the target sites. Since the AAV vector will integrate into the target cells, rather than producing viral particles, the subsequent spread of the vector will be minor, and mainly a function of passive diffusion from the site of injection, prior to integration. The degree of diffusion may be controlled by adjusting the ratio of vector to fluid carrier.

If a more widespread distribution of the vector across the CNS is desirable, it may be injected into the cerebrospinal fluid, e.g., by lumbar puncture.

To direct the vector to the peripheral nervous system, it may be injected into the spinal cord, or if more limited PNS distribution is sought, into the peripheral ganglia, or the flesh (subcutaneously or intramuscularly) of the body part of interest.

In certain situations the vector will be administered via an intravascular approach. For example, the vector will be administered intra-arterially (carotid) in situations where the blood-brain barrier is disturbed. Such conditions include cerebral infarcts (strokes) as well as some brain tumors. Moreover, for more global delivery, the vector will be administered during the "opening" of the blood-brain barrier achieved by infusion of hypertonic solutions including mannitol. Of course, with intravenous delivery, the user must be able to tolerate the delivery of the vector to cells other than those of the nervous system.

The vector may also be delivered intracerebroventricularly and/or intrathecally, for specific applications, including vectors expressing superoxide dismutase and neurotrophic factors for amyotrophic lateral sclerosis and Alzheimer's Disease and genes encoding enzymes of neurogenetic diseases e.g., Tay Sachs and Lesch-Nyan disease.

Additional routes of administration will be local application of the vector under direct visualization, e.g., superficial cortical application, or other non-stereotactic application.

For targeting the vector to a particular type of cell, e.g., a neuron, it is necessary to associate the vector with a homing agent that binds specifically to a surface receptor of the cell. Thus, the vector may be conjugated to a ligand (e.g., enkephalin) for which certain nervous system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the helper virus used to prepare the vector stock so that one of the encoded coat proteins is a chimera of a native AAV coat protein and a peptide or protein ligand, such that the ligand is exposed on the surface.

Whatever the form of conjugation, it is necessary that it not substantially interfere either with the integration of the AAV vector, or with the binding of the ligand to the cellular receptor.

The target cells may be human cells, or cells of other mammals, especially nonhuman primates and mammals of the orders Rodenta (mice, rats, rabbit, hamsters), Carnivora (cats, dogs), and Arteriodactyla (cows, pigs, sheep, goats, horses).

Gene Expression

When the exogenous DNA comprises an expressible gene the gene may be one which occurs in nature, a non-naturally occurring gene which nonetheless encodes a naturally occurring polypeptide, or a gene which encodes a recognizable mutant of such a polypeptide. It may also encode an mRNA which will be "antisense" to a DNA found or an mRNA normally transcribed in the host cell, but which antisense RNA is not itself translatable into a functional protein.

The precise nature of regulatory regions needed for gene expression may vary from organism to organism, but in general include a promoter which directs the initiation of RNA transcription. Such regions may include those 5'-non-coding sequences involved with initiation of transcription such as the TATA box. The promoter may be constitutive or regulatable. Constitutive promoters are those which cause an operably linked gene to be expressed essentially at all times. Regulatable promoters are those which can be activated or deactivated. Regulatable promoters include inducible promoters, which are usually "off" but which may be induced to turn "on", and "repressible" promoters, which are usually "on" but may be turned off. Many different regulators are known, including temperature, hormones, heavy metals, the product of the natively lined gene, and regulatory proteins. These distinctions are not absolute; a constitutive promoter may be regulatable to some degree.

The regulatability of a promoter may be associated with a particular genetic element, often called an "operator", to which an inducer or repressor binds. The operator may be modified to alter its regulation. Hybrid promoters may be constructed in which the operator of one promoter is transferred into another.

The promoter may be an "ubiquitous" promoter active in essentially all cells of the host organism, e.g., the beta-actin or optomegalovirus promoters, or it may be a promoter whose expression is more or less specific to the target cells. Preferably, the tissue-specific promoters are essentially not active outside the nervous system, and the activity of the promoter optionally may be higher in some components of the nervous system than in others.

Thus, the promoter may be one which is active primarily in the central nervous system, or primarily in the peripheral nervous system, or it may be significantly active in both. If it is active in the CNS, it may be specific for the spinal cord, the brainstem (medulla, pons, midbrain, or combinations thereof), the cerebellum, the diencephalon (thalamus and/or hypothalamus), the telencephalon (the corpus striatum and/or the cerebral cortex, and, if the latter, the occipital, temporal, parietal and/or frontal lobes), or combinations thereof. The specificity may be absolute or relative.

Similarly, the promoter may be specific for particular cell types, such as neurons or glial cells in the case of the CNS, or particular receptors or effectors in the case of the PNS. If it is active in glial cells, it may be specific for astrocytes, oligodendrocytes, ependymal cells, Schwann cells, or microglia. If it is active in neurons, it may be specific for particular types of neurons, e.g., motor neurons, sensory neurons, or interneurons.

In general, to find a tissue-specific promoter, one identifies a protein which is expressed only (or primarily) in that tissue, and then isolates the gene encoding that protein. (The gene may be a normal cellular gene, or a viral gene of a virus which infects that cell). The promoter of that gene is likely to retain the desired tissue-specific activity when linked to another gene.

The tissue specificity of a promoter may be associated with a particular genetic element, which may be modified, or transferred into a second promoter.

Control of expression to specific cell types will be obtained using gene expression control elements. Specifically, one may use these approaches:
(1) Expression in All Cell Types:
Both strong viral (e.g. immediate early CMV, available on plasmid pCDNA1 from Invitrogen, Inc., San Diego, Calif.) and relatively non-specific cellular promoters (e.g., β-actin, Genbank HUMACTBET, K00790) may be used to direct expression in all cell types.
(2) Neuronal Specific Expression:
Approaches will include the use of neuron specific promoters e.g., neuron specific enolase (EMBL HSENO2, X51956), AADC, neurofilament (Genbank HUMNFL, L04147), synapsin (Genbank HUMSYNIB, M55301), and serotonin receptor (Genbank S62283), promoters, as well as the combination of more broadly active promoters together with silencer elements which restrict expression to neurons.
(3) Glial Specific Expression:
Approaches will include use of the glial fibrillary acidic protein (GFAP) promoter (Genbank HUMGFAP, J04569), S100 promoter (Genbank HUMS100AS, M65210), and glutamine synthase (EMBL HSGLUS, X59834) promoter.
(4) Expression May Be Restricted to Specific Neuronal Subpopulations Using the Following Genetic Elements:
Peptidergic promoters: e.g., enkephalin (Genbank HUMENKPH1, K00488), prodynorphin, somatostatin (Genbank RATSOMG, J00787; Genbank HUMSOMI, J00306); monoaminergic promoters: tyrosine hydroxylase (Genbank M23597), dopamine β-hydroxylase (Genbank RATDBHDR, M96011), PNMT (EMBL HSPNMTB, X52730); for cholinergic neurons: choline acetyltransferase promoter (Genbank HUMCHAT1, M89915; EMBL HSCHAT, X56585).

For the gene to be expressible, the coding sequence must be operably linked to a promoter sequence functional in the target cell. A promoter region would be operably linked to a coding sequence if the promoter were positioned. so that, when the promoter was activated, the coding sequence was transcribed. The coding sequences are operably linked if the linkage does not cause an error in the reading of the downstream sequence. In order to be "operably linked" it is not necessary that two sequences be immediately adjacent to one another.

If desired, the non-coding region 3' to the gene sequence coding for the desired RNA product may be obtained. This region may be retained for its transcriptional termination regulatory sequences, such as those which provide for termination and polyadenlylation. Thus, by retaining the 3'-region naturally contiguous to the coding sequence, the transcriptional termination signals may be provided. Where the transcriptional termination signals natively associated with the coding sequence are not satisfactorily functional in the expression host cell, then a different 3' region, functional in the host cell, may be substituted.

An "expression vector" is a vector which (due to the presence of appropriate transcriptional and/or translational control sequences) is capable of expressing a DNA molecule which has been cloned into the vector and of thereby producing an RNA or protein product encoded by an expressible gene provided by said DNA. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, when a eukaryotic expression vector is employed, e.g., for genetic manipulation prior to gene delivery, then the appropriate host cell would be any eukaryotic cell capable of expressing the cloned sequences.

In addition to or instead of an expressible gene, the nucleic acid may comprise sequences homologous to genetic material of the target cell, whereby it may insert itself into the genome by homologous recombination, thereby displacing a coding or control sequence of a gene or deleting a gene altogether, provided that these sequences do not substantially interfere with integration of AAV.

In another embodiment, the nucleic acid molecule is "antisense" to a genomic or other DNA sequence of the target organism (including viruses and other pathogens) or to a messenger RNA transcribed in cells of the organisms, which hybridizes sufficiently thereto to inhibit the transcription of the target genomic DNA or the translation of the target messenger RNA. The efficiency of such hybridization is a function of the length and structure of the hybridizing sequences. The longer the sequence and the closer the complementarily to perfection, the stronger the interaction. As the number of base pair mismatches increases, the hybridization efficiency will fall off. Furthermore, the GC content of the packaging sequence DNA or the antisense RNA will also affect the hybridization efficiency due to the additional hydrogen bond present in a GC base pair compared to an AT (or AU) base pair. Thus, a target sequence richer in GC content is preferable as a target.

It is desirable to avoid antisense sequences which would form secondary structure due to intramolecular hybridization, since this would render the antisense nucleic acid less active or inactive for its intended purpose. One of ordinary skill in the art will readily appreciate whether a sequence has a tendency to form a secondary structure. Secondary structures may be avoided by selecting a different target sequence.

In still another embodiment, the gene encodes a ribozyme, i.e., an RNA with a desirable enzymatic activity.

Summary of Examples

Current approaches to transfer genes into the nervous system employ either recombinant viral vectors which retain viral genes or defective vectors containing residual and potentially dangerous helper viruses. Adeno-associated viral (AAV) vectors are non-pathogenic integrating DNA vectors in which all viral genes are removed (96% of the viral genome) and helper virus is completely eliminated. An AAV vector expressing β-galactosidase was stereotactically injected into rat brain regions including striatum, hippocampus and substantia nigra. Vector DNA and transduced gene expression was detected from 1 day to 3 months post-injection. A second vector expressing human tyrosine hydroxylase (TH) was generated. This vector (AAVth) was injected into the denervated striatum of unilateral 6-hydroxydopamine-lesioned rats and TH immunoreactivity was obtained in striatal cells, including both glia and neurons, to 4 months. There was no evidence of pathology or toxicity in any animal treated with AAV vectors. Initial data indicates that TH transduction in the striatum via an AAV vector yields significant behavioral recovery in lesioned rats compared with AAVlac controls.

MATERIALS AND METHODS

Plasmids: Plasmid pSub201 (Samulski et al (1989) *J. Virol.* 63:3822–28) was digested with XbaI to remove nearly the entire AAV genome, leaving only the terminal repeats. A CMV promoter-lacZ gene-SV40 polyA signal cassette was isolated from plasmid pHCL (Kaplitt et al (1991) *Mol. Cell. Neurosci.* 2:320–30) by digestion with SpeI and XbaI, and this was inserted into XbaI-digested pSub201 to create pAAVlac. A second plasmid was created (pAAV-CMV-polyA) by digestion of pAAVlac with HindIII and XbaI to remove the lacZ gene and polyA signal, followed by insertion of a HindIII-XbaI fragment from pREP4 (Invitrogen), containing a polylinker and SV40 polyA signal. This plasmid was then digested with HindIII and BamHI, followed by insertion of a human tyrosine hydroxylase (hTH) cDNA (O'Malley et al (1987) *Biochemistry* 26:6910–14) in order to create pAAVth.

Creation of Defective Viral Vectors: In order to create AAV vectors, plasmids (pAAVlac or pAAVth) were transfected via the calcium phosphate method (Graham et al (1973) *Virology* 52:496–67) into 293T cells, a variant of 293 cells (Graham et al (1977) *J. Gen. Virol.* 36:59–74), (obtained from D. Baltimore) which constitutively express both the adenovirus E1a protein and the SV40 T antigen. The vector plasmids were co-transfected along with the helper plasmid pAd8, which provides necessary replication and structural proteins. The next day, cells were infected with adenovirus strain dl309 (Jones and Shenk (1978) *Cell* 13:181–88)(obtained from Thomas Shenk, Princeton University). Following full cytopathic effect, virus was harvested by multiple freeze/thaw cycles. Viral stocks were then heated to 56° C. for 30 minutes in order to inactivate residual adenovirus (Samulski et al 1989). Vector titers were obtained by histochemical assay for X-gal (Kaplitt et al (1991) *Mol. Cell. Neurosci.* 2:320–30) or immunocytochemical identification of hTH expression in 293T cells infected with serial dilutions of the vector stock, using a monoclonal anti-hTH antibody (Boehringer Mannheim) and the ABC elite detection system (Vector Labs).

Immunocytochemistry and X-Gal Histochenlistry: For analysis of brain sections from animals injected with AAVlac, tissues were fixed by intracardiac perfusion with 2% paraformaldehyde/5 mM EGTA/2 mM $MgCl_2$ in 0.1 M HEPES (pH 7.3). The addition of EGTA eliminates any background staining due to endogenous cellular enzymes. Tissue culture cells were fixed with 2% formaldehyde/0.2% glutaraldehyde in PBS (pH 7.2). X-gal histochemistry for detection of β-galactosidase expression was performed as described previously.

In Situ PCR: Brain sections were placed in detergent buffer (0.01% sodium deoxycholate/0.02% NP-40 in PBS) for 1 hour. Following PBS wash, sections were dehydrated in alcohol and 200 μl of PCR reaction buffer was added to each slide (PCR reaction buffer: 1× PCR buffer/1 μM each primer/1M $MgCl_2$/10 μl digoxigenin-dUTP (Boehringer)). Primers specific for the lacZ gene are as follows:

N-terminal - 5' to 3' CCGACTGATGCCTTCTGAACAA (SEQ ID NO: 1) (referred to as lacZ 182) The downstream primer again 5' to 3'

GACGACAGTATCGGCCTCAGGA (SEQ ID NO:2) (lacZ 560).

Slides were coverslipped and coverslips were anchored on one side with nail polish. Slides were placed on aluminum foil on the block of a thermal cycler, and the temperature was raised to 82° C. Coverslips were raised, 2 μl of enzyme mix (1× PCR buffer/2 U/ml Taq) was added to each slide and coverslips were dropped. Slides were covered in mineral oil, and the following profile was run: 35 cycles of 2 minutes, 55° C.; 2 minutes, 72° C.; 2 minutes, 94° C. Slides were placed in xylene to remove the mineral oil, and sections were re-hydrated. PCR product was detected in situ with an alkaline phosphatase-labelled anti-digoxigenin antibody, according to the manufacturer's instructions.

Animals and Tissue Preparation: Male Sprague-Dawley rats were used in all studies. Animals were treated according to the NIH Guidelines for Animal Care and Use. For surgical procedures, animals were anesthetized with a mixture of enflurane and $NO_2$. Stereotaxic microinjection was used for all brain region injections, and coordinates were determined according to the atlas of Paxinos and Watson, *The Rat Brain in Stereotaxic Coordinates*, (Academic Press, Sydney, Australia: 1982). Tissue for immunocytochemistry was removed and quickly frozen mounting medium. 5 µm sections were taken with a cryostat, and sections were fixed in buffered formalin. Tissue for X-gal histochemistry was prepared as described above.

Unilateral Substantia Nigra Lesioning: Unilateral nigral lesions were generated using the method of Perese et al (1989) *Brain Res.* 494:285–93, as previously described, During et al (1992) *Exp. Neurol.* 115:193–99. In brief, male Sprague Dawley rats 290–310 grams were anesthetized with xylazine/ketamine and placed in a Kopf stereotactic frame. The skull was exposed and burr holes drilled above the left substantia nigra, Lambda +3.5, L 2.15. Freshly made 6-hydroxydopamine (4 µg in 2 µl of 0.1% ascorbic acid in PBS) was loaded into a Hamilton syringe which was lowered into two sites over 2 minutes. The coordinates of the medial site was lateral 1.9 and ventral 7.1 mm with the needle bevel facing rostrally, whereas the lateral site is 2.3 mm lateral and 6.8 mm in the dorsal ventral plane with the needle bevel oriented laterally (Graham et al. (1977) *J. Gen. Virol.* 36:59–74). At each site 2µl was injected over 5 minutes and the needle left in place for a further 5 minutes before being withdrawn over an additional 5 minutes.

Behavioral Testing: Rats were tested 10–16 days following the 6-OHDA injections. They were placed in a hemispherical rotameter and the total number of complete body turns was recorded from 15–20 minutes following the administration of apomorphine (1 mg/kg) as described by Hefti et al. (1980), *Brain Res.*, 195:123–27. A minimum of three tests separated by at least 2 weeks was used to generate a basal rotation rate. Animals which consistently exhibited stable (less than 25% variation) asymmetrical rotational behavior of greater than 10 turns per minute were randomly selected for either AAVlac or AAVth injection.

Stereotactic injection of AAVlac or AAVth in 6-OHDA lesioned rats: Rats meeting the above behavioral criteria of a near complete lesion were anesthetized with ketamine/xylazine (70 mg/7 mg per kg) and placed in a kopf stereotactic frame. The skull was exposed and holes drilled above the denervated striatum (left) at Paxinos & Watson coordinates of AP 0.2, L 2.6 and AP 1.5, L 2.0 and L 3.0. Either AAVlac of AAVth was injected slowly using a Hamilton syringe into each of three sites at a DV depth of 5 mm. Each injection volume was 2µl. Rats were tested for apomorphine-induced rotational behavior at one and two months following surgery.

TH, NF and GFAP Immunocytochemistry: For immunohistochemical (IHC) analysis of brain sections, rats were deeply anesthetized with chloral hydrate and followed by intracardiac perfusion with IM PBS (pH=7.3) followed by 4% paraformaldehyde (PF). Brains were removed and postfixed (3–4 hours) in 4% PF followed by ascending sucrose solutions (10/15/30% in PBS) as cryoprotectant. Sections (7–30 mm) were cut in a cryostat (Reichert-Jung) and mounted on polylysine-coated slides. We used a double labelling protocol for the co-detection of TH positive cells in specific neuronal or glial subpopulations. Sections were initially incubated in blocking buffer (5% Goat Serum (GS)/5% Normal Horse Serum (NHS) in 1 M Phosphate Buffer Saline (PBS). Sections were than incubated in primary antibodies diluted in blocking buffer (mouse anti-TH [Boehringer Mannheim, 1:200], mouse anti-NF [Sigma, 1:400], rabbit anti-TH [Chemicon International, 1:3000] rabbit anti-GFAP [gift from Dept. of Pathology, Memorial Hospital, 1:800]), at room temperature (2–4 hours), rinsed in blocking buffer and incubated in secondary antibodies (mouse anti-texas red [vector, 1:75 or biotinylated rabbit anti-IgG [vector, 1:400]) at room temperature (1 hour). Sections were washed in PBS and incubated at room temperature (1 hour) in avidin-neutralite FITC [Molecular Probes Inc, 1:400]. Slides were coverslipped with PBS/Glycerol (0.05:1) and kept at −20° C.

EXAMPLE 1

Creation of an Adeno-associated Virus (AAV) Vector for Gene Transfer Into Brain.

Figure 2:
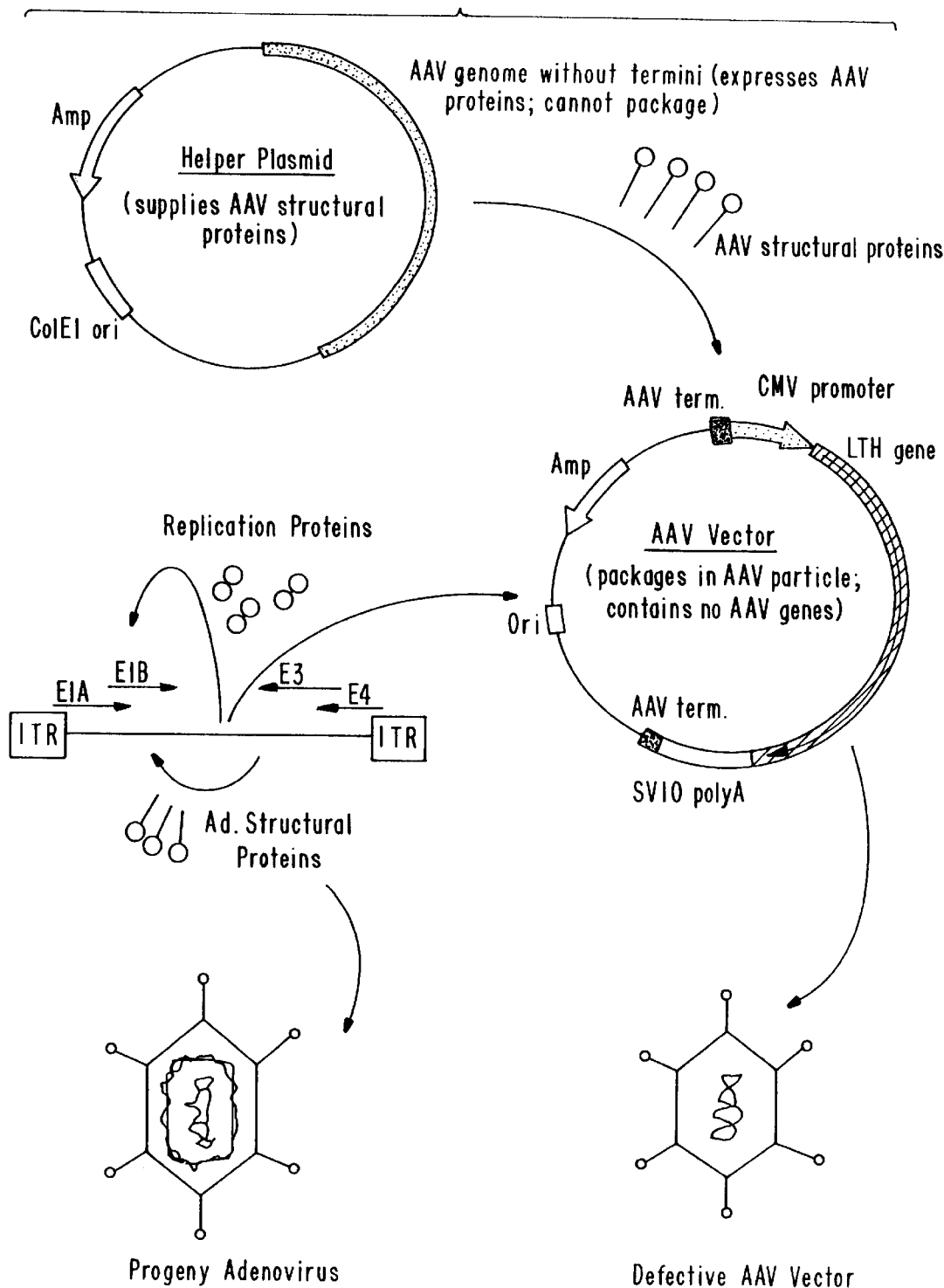
FIG. 2 is a schematic diagram outlining the relationship of the helper plasmid, AAV vector, adenovirus helper, etc.

The bacterial lacZ gene was inserted into plasmid psub201 (Samulski et al (1989) *J. Virol.* 63:3822–28) between the termini of the AAV genome. These termini contain the recognition signals for cleavage and packaging into an AAV vector. The lacZ gene encodes the bacterial enzyme β-galactosidase, which produces an insoluble blue precipitate upon reaction with the appropriate substrate. The human cytomegalovirus (CMV) immediate-early promoter was used to direct gene expression, and an SV40 polyadenylation signal was placed downstream of the lacZ gene (FIG. 1). Cells were transfected with pAAVlac and a second plasmid, pAd8 (Samulski et al. 1989), which provides AAV structural proteins but lacks AAV termini and thus cannot package into virus. Co-transfected cells were then infected with adenovirus type 5 (Jones and Shenk (1978) *Cell* 13:181–188) to provide remaining replication and packaging machinery (FIG. 2). The resulting stock consisted of packaged AAV-lac vectors (AAVlac) and progeny helper adenovirus; helper virus was then eliminated by heating at 56° C. for 30 minutes. The complete elimination of adenovirus was confirmed by the inability to detect any viral plaques in cultured cells 1 week following infection with this viral stock. AAV vectors were then titered by infection of cultured 293 cells, histochemical staining for β-galactosidase expression and counting of blue cells. There was no difference in the number of cells observed at 1 and 5 days following infection, demonstrating an absence of vector replication and spread. When the process was repeated using a lacZ plasmid without the AAV recognition signals, no positive cells were observed following infection with the resulting stock. This indicates that the lacZ gene was packaged into an AAV virus which was incapable of autonomous replication while residual adenovirus was completely eliminated.

EXAMPLE 2

AAV Vectors Can Transfer and Stably Express A Foreign Gene in The Adult Rat Brain AAVlac was stereotaxically microinjected into various regions of the adult rat brain, including caudate nucleus, amygdala, striatum and hippocampus. Animals were initially sacrificed between 1 and 3 days following injection and sections were processed for X-gal histochemistry. Positive cells were demonstrated within each region. The efficiency of gene transfer into the brain appeared to be at least equivalent to that observed previously with HSV or adenovirus vectors.

In order to analyze the long-term stability of AAV gene transfer and expression within the mammalian brain, animals were injected in the caudate nucleus with AAVKlac and sacrificed 2–3 months following surgery. First, the polymerase chain reaction (PCR) was adapted for use within brain sections to permit amplification and visualization of viral vector DNA in situ. See Nuovo et al (1991) *Am. J. Pathol.* 139:1239–44; Nuovo et al (1993) *PCR Meth*, 2:305–12; Flotte et al (1993) *Proc. Nat. Acad. Sci. USA* 90:10613–17. Numerous cells within the brain were detected which retained the bacterial lacZ gene after 2 months. There was no staining on the opposite side of the brain sections or in sections processed without Taq polymerase, and positive cells were also absent from brains injected with adenovirus alone. Additional animals were then sacrificed and sections were processed for X-gal histochemistry (See Kaplitt et al (1991) *Mol. Cell. Neurosci.* 2:320–30) in order to identify cells containing functional $\mu$-galactosidase. Positive cells were identified within injected regions of the caudate nucleus up to 3 months following vector injection. At no time were behavioral or physiological abnormalities detected within the animal subjects, and the brain sections showed no evidence of pathology resulting from the AAV gene transfer.

EXAMPLE 3

The AAV Vector Yields Expression of Tyrosine Hydroxylase in the Caudate Nucleus of 6-OHDA Lesioned Rats Parkinson's Disease (PD) is a neurodegenerative disorder characterized by loss of the nigrostriatal pathway and is responsive to treatments which facilitate dopaminergic transmission in the caudate-putamen. (Yahr and Bergmann, *Parkinson's Disease* (Raven Press, 1987), Yahr et al. (1969) *Arch. Neurol.* 21:343–54. In experimental animals, genetically modified cells that express tyrosine hydroxylase, and thereby synthesize dihydroxyphenylalanine (L-Dopa), induce behavioral recovery in rodent models of PD. (Wolff et al. (1989) *PNAS (USA)* 86:9011–14; Freed et al (1990) *Arch. Neurol.* 47:505–12; Jiao et al (1993) *Nature* 262:4505). An alternative approach is that of direct in vivo somatic cell gene transfer whereby the intrinsic cells of the neostriatum are converted into L-Dopa-producing cells by transduction with a vector expressing TH. An HSV-1 vector expressing TH has shown that this approach may be a viable alternative to tissue transplantation. (During et al. (1992) *Soc. Neurosci Abstr.* 18:331–8). However, HSV-1 vectors currently have several limitations as described above. In order to generate a vector which may have therapeutic utility in human PD patients, we inserted a human TH cDNA (form II) (O'Malley et al. *Biochemistry* 26:6910–14) into our AAV vector (AAVth). AAVth was packaged and helper virus was eliminated as described above for AAVlac.

Figure 3:
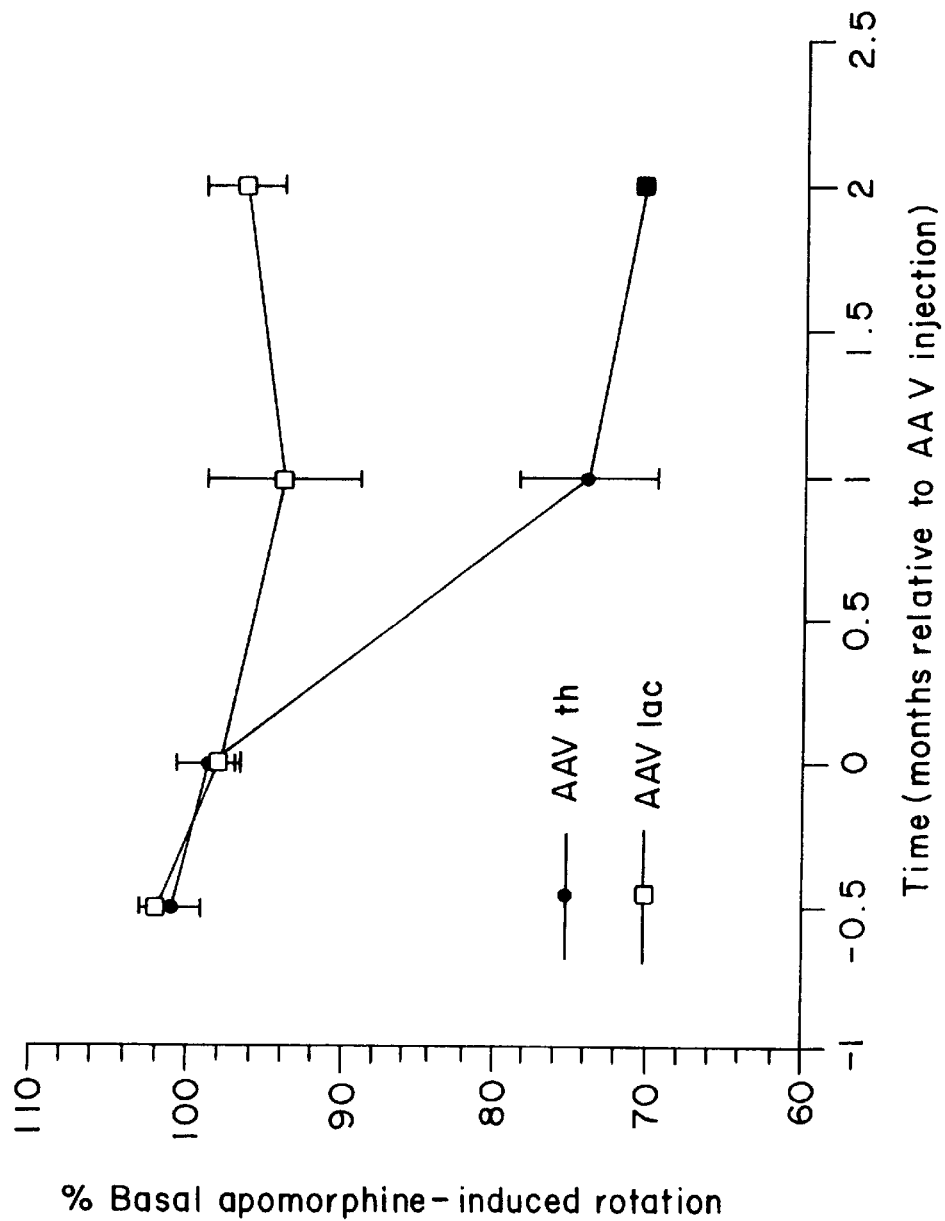
FIG. 3 shows the effect of intrastriatal AAVth or AAVlac on apomorphine-induced rotational behavior in the rodent model of Parkinson's disease.
Figure 4A:
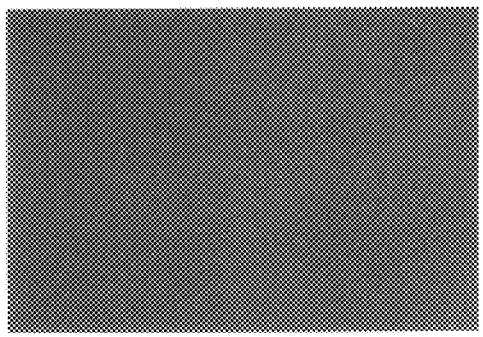
FIG. 4 shows the immunohistochemical detection of hTH expression within the caudate nucleus of 6-OHDA lesioned rats following injection of AAVth. A, Absence of immunostaining in caudate following injection of AAVlac. No staining was ever observed in AAVlac animals, and staining was also always absent from the uninjected caudate from AAVth animals. B, C, TH expression in cells of the caudate nucleus 4 months following injection of AAVth. These sections were 30 μm in thickness, which prevented morphological identification of positive cells. Approximately 30 cells are seen at the site of injection (B) and cells are also seen 2 mm away from the injection site (C), although fewer cells are present at 2 mm. This observation was repeated twice at 4 months following injection, while comparable results were obtained from 3 animals at 2 months and 2 animals at 1 month following injection. D, TH expression in caudate 1 week following AAVth injection. This section was 7 μm in thickness, revealing the neuronal appearance of the majority of positive cells. 50 positive cells can be seen in this section, which is representative of approximately 50 consecutively positive sections obtained from each short-term animal. Fewer cells were observed as far as 280 sections (2 mm) away from the injection site. This result was repeated twice at 1 week following injection, and comparable results were obtained from 9 animals at 48 hours and 9 animals at 24 hours post-injection. E,F, Double-label immunocytochemistry demonstrating neuronal TH expression. E, TH expression in a caudate cell (arrow) was revealed using a FITC-labelled secondary antibody. F, Neuronal identification of the TH-expressing cell (arrow) was obtained by sequentially staining the same section with an anti-neurofilament antibody and visualization with a Texas red-conjugated secondary antibody. Magnification: A–D, 400× E,F, 630×.
Figure 4B:
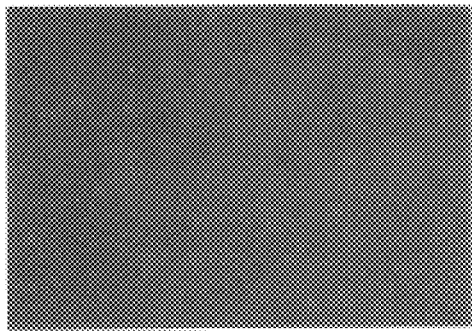
Figure 4C:
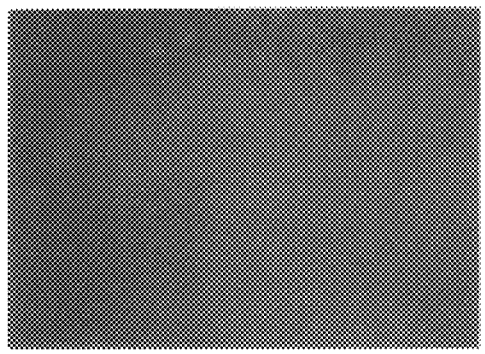
Figure 4D:
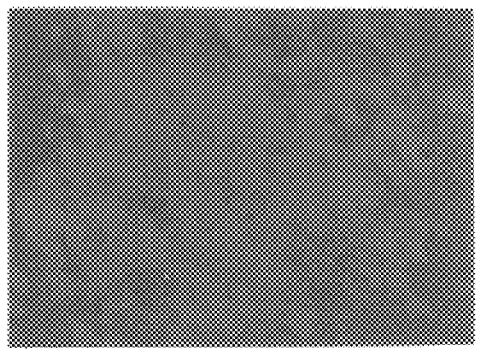
Figure 4E:
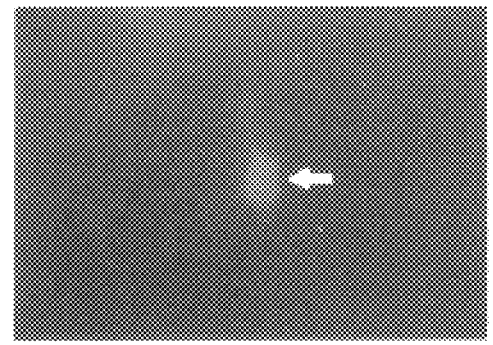
Figure 4F:
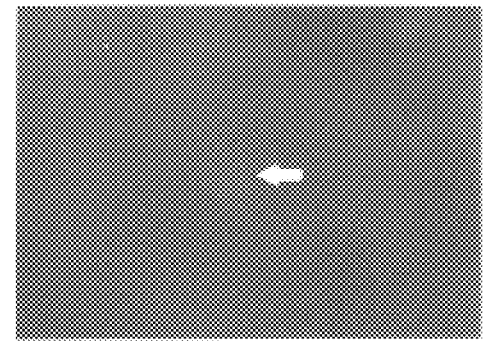
Figure 5:
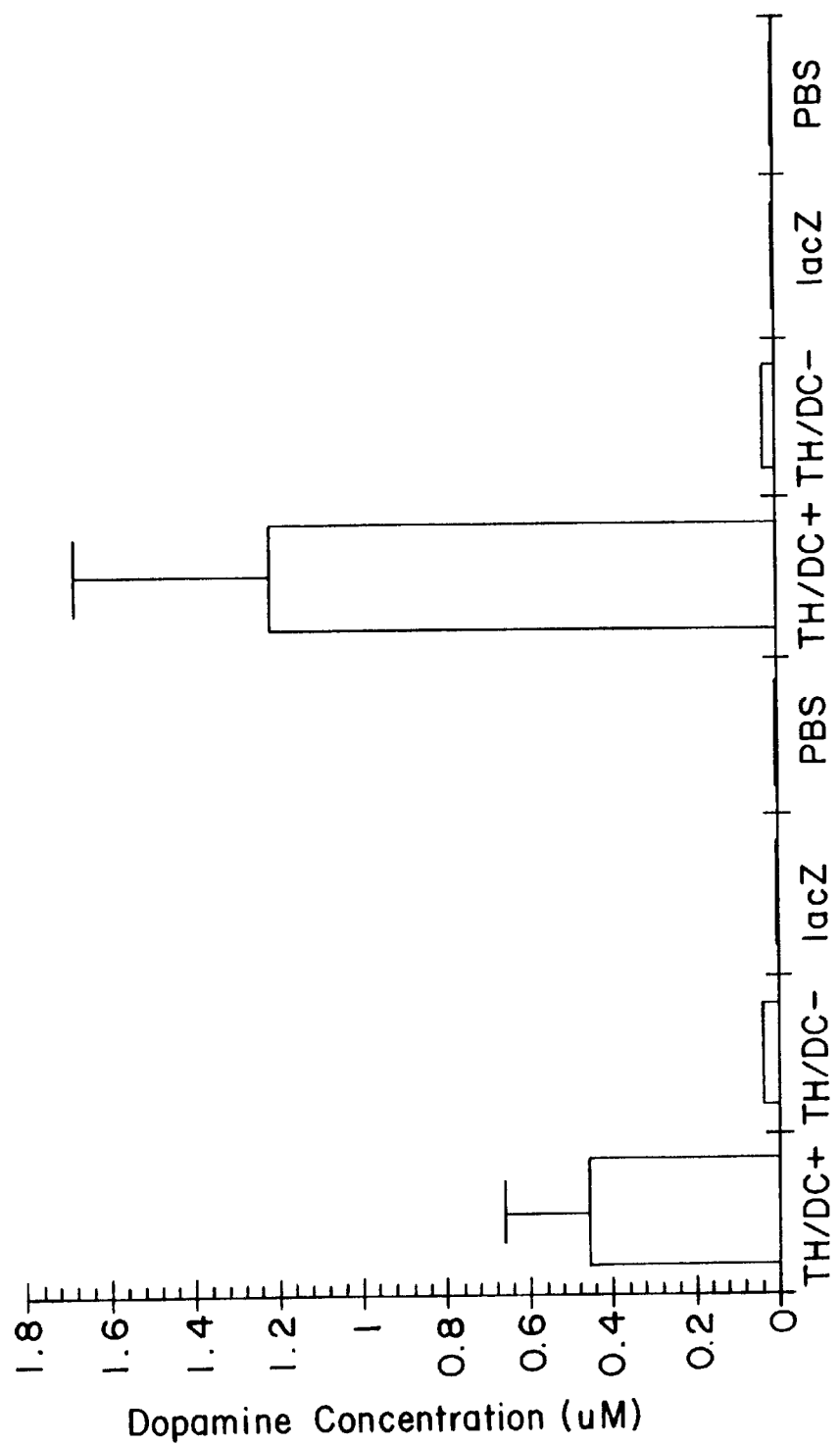
FIG. 5 shows plasmid pAAV-FlagTH-AADC. This bicistronic construct contains the bicistronic construct with open reading frames for truncated tyrosine hydroxylase containing the N-terminal Flag epitope (Flag-TH) and aromatic amino acid decarboxylase (AADC). TH converts tyrosine to L-Dopa, and then AADC converts L-Dopa to dopamine. Between the two open reading frames is a sequence allowing ribosome re-entry and initiation of translation of a second open reading frame downstream from a translational stop codon. This is the internal ribosome entry site (IRES). These are transcribed as a single messenger RNA from the human cytomegalovirus immediate early gene promoter (CMV promoter). At the 3' end of the insert is a signal for polyadenylation of the mRNA derived from the SV40 virus (SV40 polyA). The entire insert is flanked by terminal repeats from the adeno-associated virus (AAV term.), which permits replication, excision and packaging of the insert in the presence of proteins provided by the helper plasmid pAAV/Ad and helper adenovirus. The plasmid also contains standard plasmid sequences which permit replication and amplification of the DNA inside a bacterium (ori) and selection of bacterial colonies harboring the plasmid through resistance to ampicillin (amp). One of the several unique features of the AAV vector is that unlike other defective viral vectors, these plasmid sequences are lost when the DNA between the AAV termini is packaged.

Unilateral 6-hydroxydopamine lesions of the substantia nigra have been used to generate an established rodent model of PD. In this model, the asymmetry caused by differing postsynaptic receptor sensitivities between the denervated and intact striatum results in rotational behavior following systemic administration of dopaminergic agents, such as apomorphine (Hefti et al. (1980) *Brain Res.* 195:123–7). The rate of asymmetrical rotation is directly related to the severity of the striatal dopamine deficit. and this model has predictive ability in defining treatments which have therapeutic efficacy in PD. (Freed et al. (1987) *Ann. Neurol.* 8:510–19; Hargraves et al (1987) *Life Sci.* 40:959–66). Lesioned rats were tested for apomorphine-induced rotation every two weeks on a minimum of three occasions, and animals that satisfied behavioral criteria of >95% lesion efficacy (>10 rotations/minutes) were identified (Hefti et al. 1980). AAVth or AAVlac virus, or vehicle alone (phosphate buffered saline, [PBS]), was delivered by stereotactic injection into the denervated striatum. Animals were tested for apomorphine-induced asymmetrical rotation at 2, 4 and 9 weeks. The rotational behavior of the AAVlac injected animals was similar to the PBS injected animals. In contrast, AAVth injected animals demonstrated significant behavioral recovery (FIG. 3), compared to AAVlac or PBS injected groups (control groups). The average behavioral recovery caused by AAVth was 31±6% at 4 weeks and was maintained at 32+3% at 9 weeks (P<0.01) after injection.

In order to examine virally encoded TH gene expression following transduction with AAVth, animals were analyzed at times ranging from 24 hours to 7 months after injection. Expression of TH from the AAV vector was detected using immunocytochemistry with a mouse monoclonal anti-TH antibody. Although this antibody does not distinguish between the rat and human protein, TH is not expressed within either the intrinsic neurons or glia of the rat striatum (Chatterjee et al. (1992) *Science* 258:1485–88). Furthermore, endogenous TH immunoreactivity (TH-IR) within the striatum is limited to the dopaminergic afferent fibers in unlesioned animals and is absent in the completely denervated striatum. In both control and AAVlac-injected rats there was no striatal TH immunoreactivity (TH-IR) on the denervated side. In contrast, in the denervated striata injected with AAVth, numerous TH-IR cells were clustered around the injection site and extending to 2 mm away from the injection. The majority of cells within the striatum appeared to be neurons morphologically, and double-labelling with both the anti-TH monoclonal antibody and an anti-neurofilament antibody confirmed that a substantial number of intrinsic striatal neurons expressed immunoreactive TH de novo. Additional sections were then double labelled with bOth the TH monoclonal antibody and a rabbit polyclonal antibody to glial fibrillary acidic protein (GFAP), a marker of astrocytes and oligodendrocytes. Other sections were double labelled with TH antibody and antibodies for glutamic acid decarboxylase (GAD), a marker of GABAergic neurons, the predominant neuronal population of the neostriatum. Double labelling revealed that the majority of TH-IR cells were immunoreactive for GAD, while a small percentage of TH-IR cells were GFAP positive. GABAergic neurons constitute approximately 95% of the intrinsic striatal neuron population with choline acetyl transferase (ChAT, cholinergic) positive cells making up the remainder. Double labelling with TH and ChAT also revealed expression of vector encoded TH in striatal cholinergic neurons.

The titre of the AAVth stock used for these in vivo studies was $5\times10^6$ infectious particles (i.p.)/ml. Therefore a single injection of 2 $\mu$l would result in 10,000 positive cells if the efficiency of infection was 100% and each i.p. infected a different cell. However, as previous infection of AAV does not prevent subsequent re-infection or multiple particles infecting the same cell, in the immediate vicinity of the injection we might expect cells to have multiple infection. Moreover, AAVth might also infect axons and terminals and following retrograde transport be expressed in the cell body regions of the striatal afferents (e.g., the surviving dopamine nigral neurons, the cortex, reticular nucleus of the thalamus and dorsal raphe nuclei). In the AAVth-injected animals, the total number of striatal cells containing TH-IR consistently exceeded 1000 for each of the 2 $\mu$l injections suggesting a minimum of 10% in vivo efficiency, significantly greater than previous observations using defective HSV-1 vectors (@2%). Moreover, the level of expression was also examined at times ranging from 3 days to 7 months. Expression persisted throughout this 7 month period, although the level of expression diminished by approximately 50%.

Furthermore there were no signs of cytopathic effects. The only changes observed in the short term animals (examined less than 1 week following injection) was a slight needle injury at the injection site which was similar in PBS-injected and AAVlac-injected animals. In the long-term animals (greater than two months), the residual needle track was not consistently visible and there was no evidence of any neuronal injury or reactive gliosis. There were also no behavioral or gross pathological signs of brain damage in any subject.

EXAMPLE 4

Expression of Two Genes From A Single AAV Vector Results in de novo Synthesis of the Neurotransmitter Dopamine Dopamine synthesis is catalyzed by two enzymes, TH and aromatic acid decarboxylase (AADC). The reaction catalyzed by TH results in the synthesis of L-Dopa, and this is the rate-limiting step in the synthesis of dopamine. Dopamine then results from conversion of L-Dopa by AADC. Although striatum does not contain cells which endogenously produce TH, there are a small percentage of striatal cells which produce AADC. Therefore, behavioral recovery in animals treated with AAVth (or other approaches using TH alone) presumably occurs secondary to conversion of the resulting L-Dopa to dopamine by endogenous striatal AADC. Since a limited number of cells produce AADC, however, it is possible that synthesis of dopamine could be enhanced by expression of both TH and AADC in every transduced cell. In this manner, any target cell would become an autonomous dopamine-producing cell following gene transfer. Recent evidence in fact suggests that expression of both genes in the denervated striatum may be superior to expression of TH alone (Kang, et. al., 1993). Furthermore, the most substantial behavioral recovery following cell transplantation occurred when TH-expressing muscle cells were utilized (Jiao et al 1993), and unlike fibroblasts from earlier studies, muscle cells express endogenous AADC activity. This suggested that creation of an AAV vector containing both TH and AADC would be valuable.

Due to the limitation on insert sizes in AAV vectors, several modifications were required in order to create a vector containing both genes. First, the TH gene was truncated, eliminating the 5' end. Truncation of the TH gene has actually been shown to increase enzymatic activity due to removal of an amino terminal regulatory domain. (Walker et al (1994) Bioch. Biophys. Acta 1206:113–119). Therefore, this served a functional purpose as well as increasing the space available for other genetic elements. In addition, a small synthetic oligonucleotide, encoding a novel epitope, was attached to the 5' end of the truncated TH. This novel epitope, termed "Flag", is recognized by a commercially available monoclonal antibody; this provides an independent and unambiguous marker for expression of AAV-transduced TH in vivo.

After modifying TH, the AADC gene was inserted into the vector. Creation of two independent expression units, with two promoters and two polyadenylation signals, would have resulted in an insert size so large as to be incompatible with the constraints of the AAV vector. Therefore, an IRES element was inserted between the Flag-TH and AADC cDNAs. Most eukaryotic mRNAs are monocistronic; they contain a single-open reading frame, and when translation of a peptide is stopped and the ribosome falls off of the transcript, additional downstream translational start sites cannot be utilized. When the IRES element is present on an mRNA downstream of a translational stop codon, it directs ribosomal re-entry (Ghattas et al (1991) Mol. Cell. Biol. 11:5848–5959), which permits initiation of translation at the start of a second open reading frame (IRES=Internal Ribosome Entry Site). In this manner, a eukaryotic bicistronic mRNA can be created which allows translation of two distinct peptides from a single mRNA (FIG. 2). Thus, with only a single promoter (CMV) and a single mRNA polyadenylation signal (SV40) directing expression of a single transcript, translation of both the Flag-TH and AADC proteins could occur within a single cell transduced with a single AAV vector.

Figure 6:
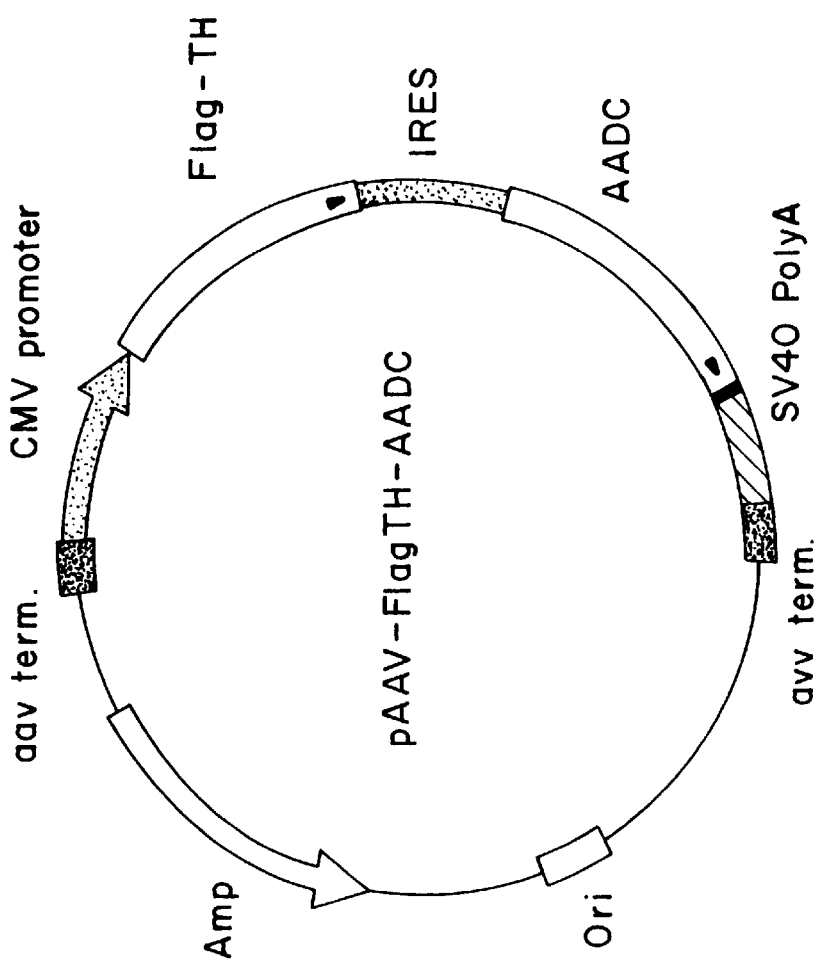
FIG. 6 shows dopamine release into culture medium following plasmid transfection in 293T cells. The first group of 4 samples represents 30 minutes following addition of tyrosine and tetrahydrobiopterin, while the second 4 samples were taken after 60 minutes. Dopamine release was significant at 30 minutes, and even higher at 60 minutes, in cells transfected with pAAV-FlagTH-AADC and given tyrosine and tetrahydrobiopterin (TH/DC+). Cells transfected with this plasmid but not given the substrate and co-factor (TH/DC−) synthesized negligible amounts of dopamine at both time points. Controls transfected with pAAVlac, expressing the bacterial lacZ gene, or mock-transfected with phosphate-buffered saline (PBS) produced no detectable amount of dopamine.

Following creation of the plasmid AAV Flag-TH/AADC, each of the independent expression parameters were tested in culture. The plasmid was transfected into 293T cells, and then the following day the substrate tyrosine and an essential co-factor (tetrahydrobiopterin) were added to the tissue culture medium of some of these cultures. For comparison, additional cells were transfected with the plasmid AAVlac or were mock-transfected. Samples of medium were obtained at 30 minutes and 60 minutes after addition of co-factors (or mock treatment), and these were analyzed for the presence of dopamine by high-performance liquid chromatography (HPLC). As indicated in FIG. 6, very high levels of dopamine were produced in 293T cells transfected with AAV Flag-TH/AADC in the presence of both co-factors. In similarly transfected cells lacking the co-factors, barely detectable amounts of dopamine were produced, while AAVlac-transfected or mock-transfected cells yielded absolutely no dopamine synthesis even in the presence of adequate co-factors. This indicated that 293T cells were incapable of endogenously directing dopamine synthesis, however introduction of the bicistronic vector AAV Flag-TH/AADC converted these cells into high level, co-factor dependent producers of dopamine. Finally, it should be noted that these cells were then fixed and stained with the anti-Flag monoclonal antibody, and this revealed highly specific histochemical detection of the Flag epitope with no background.

The specificity and function of the bicistronic AAV vector was further analyzed in cultured 293T cells. Despite the above data, it was still possible that 293T cells contained endogenous AADC activity. If this were true, then expression of Flag-TH alone would have yielded similar data without achieving translation of the second (AADC) open-reading frame. In order to test this, an additional vector was created. AAVFlag-TH contains a monocistronic insert with the Flag-TH open reading frame but lacking both the IRES sequence and the AADC open reading frame. 293T cells were then transfected with AAV Flag-TH/AADC, AAVFlag-TH, AAVlac or no plasmid. Both co-factors were added to all cultures the following day, and then samples of the medium were tested for both L-Dopa and dopamine by HPLC (Table 1). Cells which were transfected with no plasmid or AAVlac could not synthesize any detectable level of either L-Dopa or dopamine. The lack of L-Dopa demonstrated that 293T cells do not possess any endogenous TH activity. Furthermore, cells transfected with AAVFlag-TH yielded very high levels of L-Dopa, but undetectable amounts of dopamine. This demonstrates that 293T cells do not possess any AADC activity either. Furthermore, this indicates that the truncated TH is highly active and the addition of the 5' Flag sequence did not adversely influence enzymatic activity. Finally, cells transfected with AAV Flag-TH/AADC produced significant amounts of L-Dopa but very high levels of dopamine. Presumably the lower level of L-Dopa in these cells compared with those transfected with AAVFlag-TH was due to the efficient conversion of L-Dopa to dopamine. Thus two genes can be placed into a single AAV vector and techniques such as insertion of an intervening IRES sequence can result in translation of both protein products. These data also indicate that AAV vectors can yield expression of multiple, functionally active proteins which can synergize in the production of a single, biologically active neurotransmitter. The Flag epitope was also shown to be a specific, independent marker of AAV-derived TH protein production without adversely influencing TH enzymatic activity.

TABLE 1

Release of L-Dopa and Dopamine into the Culture Medium of 293T Cells Following Plasmid Transfection.

|  | L-Dopa (pg/ml) | Dopamine (pg/ml) |
| --- | --- | --- |
| Blank | <40 | <40 |
| LacZ | <40 | <40 |
| Flag-TH | 8200 | <40 |
| TH-AADC | 800 | 4050 |

Controls which were transfected with pAAVlac or mock-transfected with PBS did not produce any detectable level of either L-Dopa or Dopamine, and therefore at the very least these cells did not contain TH activity. Following transfection with pAAV-FlagTH, which expresses only tyrosine hydroxylase, significant amounts of L-Dopa were produced but none was converted to dopamine. This demonstrated that the truncated TH with the N-terminal Flag epitope was enzymatically active, yet 293T cells contain no endogenous AADC activity, hence the absence of conversion to dopamine. By contrast, cells transfected with the bicistronic vector pAAV-FlagTH-AADC yielded significant levels of L-Dopa, but far higher levels of dopamine. This demonstrated that the Flag-TH was fully active, synthesizing L-Dopa, but that functional AADC was also translated from the same mRNA, and this converted much of the L-Dopa to dopamine. Therefore, two enzymes were expressed from a single vector, thereby converting a cell with no endogenous TH or AADC activity into a dopamine-producing cell.

EXAMPLE 5

AAV Vector-mediated Gene Therapy in a Primate Model of Parkinson's Disease

The great potential of the bicistronic vector as a therapeutic agent for Parkinson's disease has led to the rapid initiation of primate studies. The primate model of Parkinson's disease is considered to be the gold-standard model for evaluation of potential therapies prior to entering human clinical trials. This model was originally developed from the observation in the early 1980s that groups of younger people were developing a neurodegenerative disorder strikingly similar to idiopathic Parkinson's disease. The source of this disorder was traced to the use of a street drug, and the specific causative agent was found to be 1-methyl-4 phenyl-1,2,3,6-tetrahydropyridine (MPTP) (Langston (1985) Trends Pharmacol. Sci. 6:375–378). When MPTP was then given to primates, the animals developed a parkinsonian disorder that has become the principle model for testing anti-parkinsonian agents. Peripherally administered MPTP will cross the blood-brain barrier, whereupon it is converted to MPP+ by monoamine oxidase B (MAO-B). This compound is then selectively concentrated within the dopaminergic neurons of the substantia nigra via an energy-dependent, presynaptic uptake mechanism. This may be enhanced by the ability of neuromelanin, found within nigral neurons, to bind MPP+ (D'Amato et al (1986) Science 231:987–989). MPP+ is a potent neurotoxin which eventually causes the degeneration of nigral dopaminergic neurons and loss of the nigro-striatal dopamine pathway, as is seen in Parkinson's disease. (Redmond et al (1993) Ann. N.Y. Acad. Sci. 695:258–266; Tipton and Singer (1993) J. Neurochem. 61:1191–1206).

Early studies initiated in MPTP primates have been designed to test the safety of the AAV system in primates and to obtain information regarding the potential therapeutic efficacy of AAV Flag-TH/AADC for Parkinson's disease. The initial study employed a small number of animals with only moderate nigral lesions and was designed to determine whether AAV vectors can transfer genes in the adult primate brain, and whether dopamine transmission could be increased in the striatum using the bicistronic vector. Purified vector was stereotaxically injected unilaterally into the striatum of MPTP-treated primates, and subjects were then sacrificed either 10 days or 4.5 months after injection. Tissue sections were analyzed for Flag immunoreactivity, and numerous positive cells were demonstrated in several sections from the injected striatum in both short and long-term subjects, while sections from the uninjected side were completely negative.

The majority of positive cells appeared morphologically to be neurons. This demonstrated for the first time that AAV vectors could successfully transfer genes into the primate brain (During et al (1994) Abstr. Soc. Neurosci. 20:1465).

Biochemical analysis of tissue samples from treated primates further indicated that the vector did cause an increase in striatal dopamine (During et al (1994)). For example, in one subject sacrificed at 10 days following treatment, the level of dopamine from a striatal tissue sample near the site of AAV injection was 18.93 ng/mg protein. An equivalent tissue sample from the uninjected, contralateral striatum yielded a dopamine level of 7.97 ng/mg protein. Tissue samples from distal sites on the injected and uninjected sides resulted in dopamine levels of 2.48 ng/mg and 2.27 ng/mg respectively. Since peripherally administered MPTP should result in roughly equal lesions to the substantia nigra bilaterally, the approximately 140% increase in dopamine levels in the injected striatum compared with the untreated side suggests that the AAV vector resulted in expression of functionally active enzymes.

A second study employed more severely lesioned primates in order to determine whether there is a therapeutic potential for AAV Flag-TH/AADC. Subjects were divided into two groups, with the treated group receiving AAV Flag-TH/AADC and controls receiving AAVlac. All animals received bilateral stereotaxic injections, with the same virus infused into the striatum on both sides of the brain. Subjects were then followed for 2.5 months after surgery. Observations suggest that the bicistronic vector resulted in sustained improvement in parkinsonian behavior (During et al (1994). Monthly assessments of control and treated animals by blinded caretakers reported virtually no change in the behavior of animals which were subsequently determined to have been controls, while the response in treated subjects varied from modest improvement to substantial recovery of function. Most of the animals began the study unable, spending much of their time face-down and requiring assistance in order to feed and groom themselves. Reports indicate that improvements in treated animals resulted in some cases in decreased time spent face-down and recovery of the ability to feed and groom themselves. These blinded observations suggest that AAV vectors may result in behavioral recovery of parkinsonian primates. It should also be noted that in both primate studies, there was no behavioral or histological evidence of toxicity due to the AAV vector. All of the data indicate that safe, long-term improvement of human neurological diseases may be possible via genetic modification of adult brain cells in vivo using AAV vectors.

EXAMPLE 6

Expression of A Growth Factor From an AAV Vector Can Yield Recovery of Function Following Neuronal Lesions An additional AAV vector has been developed as an alternative approach to the treatment of Parkinson's disease. To date, the majority of therapeutic strategies for PD have concentrated upon increasing striatal dopamine levels. Although behavioral recovery in animal models has been repeatedly demonstrated, this is not a cure for the disease but rather symptomatic palliation. Neuronal degeneration in the substantia nigra is the pathological result of the disease process, and progression of neurodegeneration is not altered by increasing striatal dopamine. Recently, however, several reports have determined that growth factors such as glial-derived neurotrophic factor (GDNF) can be protective of and trophic for neurons of the substantia nigra (Lin et al (1993) *Science* 260:1130–1132). Therefore, an AAV vector was created containing the cDNA for GDNF under the control of the CMV promoter.

Rats were lesioned with 6-OHDA and subsequently received injections AAVgdnf, AAVlac or saline into the lesioned substantia nigra (During et al (1994)). After several weeks, dopamine release into the striatum on the lesioned side was determined using intracerebral microdialysis. This technique permits sampling of local neurotransmitter release within a specific brain region of living animals (During and Spencer (1993) *Lancet* 341:1607–1610). Baseline dopamine levels were sampled three times and there was no difference between groups. Animals were then treated with potassium which induces release of dopamine from presynaptic terminals. Neither the AAVlac nor saline treated animals showed any variation in dopamine release from baseline, indicating that there were few dopaminergic terminals present within the striatum. The group treated with AAVgdnf, however, yielded an significant increase in dopamine release of 200% ($p<0.05$). Since the AAV vector only contained the gene for a growth factor, the restoration of potassium-induced dopamine release into the striatum suggests that GDNF expression either protected or promoted regrowth of dopaminergic neurons in the substantia nigra following 6-OHDA treatment.

These results were further supported by subsequent administration of nomifensine to animal subjects after dopamine levels in the AAVgdnf group returned to baseline. Nomifensine is a drug which increases synaptic dopamine levels by inhibiting dopamine-reuptake. Again both control groups showed no change in dopamine levels in response to nomifensin, while striatal dopamine increased 150% ($p<0.05$) in the group treated with AAVgdnf. Together these data demonstrate that AAV-mediated transfer of a growth factor gene can either protect or restore dopaminergic inputs to the striatum. Thus gene therapy can be useful for both palliation of PD through striatal expression of synthetic enzymes for dopamine as well as for treatment of the underlying disease process by expressing growth factors which may protect or regenerate dopaminergic neurons. The present invention is the first demonstration that AAV vectors can safely and efficiently transfer and express a foreign gene marker gene (lacZ) in the adult rat brain. Furthermore, stability of viral DNA and lacZ expression within the brain was observed for at least 7 months with no evidence of pathology or toxicity. Expression of human tyrosine hydroxylase (hTH) was demonstrated in both neurons and glia of rat brains which had previously received unilateral 6-hydroxydopamine (6-OHDA) lesions in the substantia nigra. These lesions result in asymmetrical (contralateral to the side of the lesion) rotational behavior when rats are treated with apomorphine, and this has been used as a behavioral model of Parkinson's disease (PD). Following vector injection into the caudate nucleus, expression of hTH was demonstrated up to 7 months later, and preliminary evidence indicates that sustained expression of hTH from an AAV vector can reduce rotational behavior following 6-OHDA administration.

What is claimed is:

1. A method of delivering to a mammalian nervous system target cell a DNA that is expressed in the target cell for greater than 3 months comprising administering an adenoassociated virus-derived (AAV) vector to the target cell, wherein said vector transduces the target cell; and wherein said vector is free of both wildtype and helper virus and has been modified to comprise a DNA which is exogenous to an adeno-associated virus.

2. The method of claim 1 wherein the DNA comprises an expressible gene and said gene is expressed in said target cell either constitutively or under regulatable conditions.

3. The method of claim 2 wherein the expressible gene encodes a messenger RNA which is antisense with respect to a messenger RNA transcribed from a gene endogenous to said cell.

4. The method of claim 2 wherein the expressible gene encodes a protein selected from the group consisting of tyrosine hydroxylase and aromatic amino-acid decarboxylase.

5. The method of claim 2 wherein the expressible gene encodes a specific neurotrophic factor for mesencephalic dopaminergic neurons.

6. The method of claim 2 wherein the expressible gene encodes an enzyme which reduces the level of free radicals in said target cell when said enzyme is expressed in said target cell.

7. The method of claim 2 wherein the expressible gene encodes a protein which enhances GABAergic activity.

8. The method of claim 2 wherein the expressible gene encodes a protein which regulates an ion channel that alters neuronal excitability.

9. The method of claim 3 wherein the antisense RNA is antisense to the mRNA which is translatable into a glutamate receptor.

10. The method of claim 2 wherein the expressible gene encodes thymidine kinase.

11. The method of claim 1 Wherein the vector does not comprise any AAV gene in functional form.

12. The method of claim 1 wherein the vector retains essentially only the inverted terminal repeats of AAV.

13. The method of claim 2 wherein the expressible gene comprises a coding sequence and a regulatory sequence operably linked to said coding sequence, whereby, when said regulatory sequence is activated, a messenger RNA transcript is transcribed from said coding sequence.

14. The method of claim 13 wherein said regulatory sequence renders the expression nervous system-specific.

15. The method of claim 14 wherein the expression is central nervous system-specific.

16. The method of claim 15 wherein the expression is specific to one or more CNS components selected from the group consisting of the spinal cord, brainstem, cerebellum, diencephalon and telencephalon.

17. The method of claim 13 wherein the expression is neuron-specific.

18. The method of claim 13 wherein the expression is glia-specific.

19. The method of claim 1 wherein the target cell is a mammalian cell of a mammalian order selected from the group consisting of Primata, Rodenta, Carnivora and Arteriodactyla.

20. The method of claim 19 wherein the target cell is a human cell.

21. The method of claim 1 wherein the target cell is in cell culture.

22. The method of claim 1 wherein the target cell is in a living mammal.

23. The method of claim 20 in which the vector is delivered to essentially all nervous system cells of the mammal.

24. The method of claim 20 in which the vector is specifically delivered to particular cell types or regions of the nervous system of the mammal.

25. A method of preventing or treating a disorder of the nervous system which comprises delivering exogenous DNA, by the method of claim 1, to cells of the nervous system, said exogenous DNA being chosen so that said delivery will prevent or treat the disorder of the nervous system.

26. An AAV-derived vector which retains only the replication and packaging signals of AAV, and which comprises expressible genes encoding tyrosine hydroxylase and aromatic amino acid decarboxylase.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: YES (iv) ANTI-SENSE: NO

-continued

```
    (xi) SEQUENCE DESCRIPTION: SEQ ID NO: 1:

CCGACTGATG CCTTCTGAAC AA                                                    22

(2) INFORMATION FOR SEQ ID NO: 2:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: YES (iv) ANTI-SENSE: YES (xi) SEQUENCE DESCRIPTION: SEQ ID NO: 2:

GACGACAGTA TCGGCCTCAG GA                                                    22
```